(12) United States Patent
Salmanzadeh

(10) Patent No.: US 11,701,668 B1
(45) Date of Patent: Jul. 18, 2023

(54) METHODS AND DEVICES FOR MAGNETIC SEPARATION

(71) Applicant: 10X Genomics, Inc., Pleasanton, CA (US)

(72) Inventor: Alireza Salmanzadeh, San Ramon, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 65 days.

(21) Appl. No.: 17/314,756

(22) Filed: May 7, 2021

Related U.S. Application Data

(60) Provisional application No. 63/022,067, filed on May 8, 2020.

(51) Int. Cl.
*B03C 1/28* (2006.01)
*B03C 1/033* (2006.01)
*G01N 33/543* (2006.01)

(52) U.S. Cl.
CPC .......... *B03C 1/288* (2013.01); *B03C 1/0332* (2013.01); *B03C 1/284* (2013.01); *G01N 33/54326* (2013.01); *B03C 2201/18* (2013.01); *B03C 2201/26* (2013.01)

(58) Field of Classification Search
CPC ....... B03C 1/288; B03C 1/0332; B03C 1/284; B03C 2201/18; B03C 2201/26; G01N 33/54326; G01N 33/54333
USPC ........................................................ 209/39
See application file for complete search history.

(56) References Cited

U.S. PATENT DOCUMENTS

| | | |
|---|---|---|
| 5,658,548 A | 8/1997 | Padhye et al. |
| 5,705,628 A | 1/1998 | Hawkins |
| 5,897,783 A | 4/1999 | Howe et al. |
| 6,133,436 A | 10/2000 | Koster et al. |
| 7,718,421 B2 | 5/2010 | Chen et al. |
| 9,182,395 B2 * | 11/2015 | Tajima ............. G01N 33/54326 |
| 9,347,056 B2 | 5/2016 | Saito et al. |
| 9,839,911 B2 | 12/2017 | Weitz et al. |
| 9,975,122 B2 | 5/2018 | Masquelier et al. |
| 10,011,872 B1 | 7/2018 | Belgrader et al. |
| 10,245,587 B2 | 4/2019 | Masquelier et al. |
| 10,323,278 B2 | 6/2019 | Belgrader et al. |
| 10,544,413 B2 | 1/2020 | Bharadwaj et al. |
| 10,697,000 B2 | 6/2020 | Belgrader et al. |
| 11,135,584 B2 | 10/2021 | Masquelier et al. |

(Continued)

FOREIGN PATENT DOCUMENTS

CN 109073518 A * 12/2018 ........ B01L 3/502761
EP 1944368 A1 7/2008
(Continued)

OTHER PUBLICATIONS

U.S. Appl. No. 17/242,802, Salmanzadeh.
(Continued)

*Primary Examiner* — Gene O Crawford
*Assistant Examiner* — Muhammad Awais
(74) *Attorney, Agent, or Firm* — Clark & Elbing LLP

(57) ABSTRACT

Devices, systems, and their methods of use, for sorting or separating magnetic particles are provided. A magnetic source, e.g., with at least one sharp feature, can be employed to exert a strong magnetic field on magnetic particles in order to separate particles of a desired and predictable property.

19 Claims, 4 Drawing Sheets

(56) References Cited

U.S. PATENT DOCUMENTS

| | | |
|---|---|---|
| 2003/0027203 A1 | 2/2003 | Fields |
| 2004/0040851 A1 | 3/2004 | Karger et al. |
| 2004/0214175 A9 | 10/2004 | McKernan et al. |
| 2005/0013741 A1 | 1/2005 | a' Brassard |
| 2005/0172476 A1 | 8/2005 | Stone et al. |
| 2006/0094108 A1 | 5/2006 | Yoder et al. |
| 2006/0163385 A1 | 7/2006 | Link et al. |
| 2007/0003422 A1 | 1/2007 | Yildirim et al. |
| 2007/0077604 A1* | 4/2007 | Wyatt ............. G01N 33/54326 435/7.21 |
| 2012/0045828 A1 | 2/2012 | Davis et al. |
| 2012/0190037 A1 | 7/2012 | Durin et al. |
| 2012/0261348 A1* | 10/2012 | Roh ..................... B03C 1/288 210/695 |
| 2014/0235506 A1 | 8/2014 | Hindson et al. |
| 2015/0031037 A1 | 1/2015 | Li et al. |
| 2015/0361418 A1 | 12/2015 | Reed |
| 2016/0298107 A1 | 10/2016 | O'Farrell et al. |
| 2019/0329245 A1 | 10/2019 | Masquelier et al. |
| 2020/0115703 A1 | 4/2020 | Bharadwaj et al. |
| 2021/0032678 A1 | 2/2021 | Belgrader et al. |
| 2021/0187515 A1 | 6/2021 | Alimsijah et al. |
| 2021/0293693 A1 | 9/2021 | Bharadwaj et al. |
| 2022/0097045 A1 | 3/2022 | Masquelier et al. |

FOREIGN PATENT DOCUMENTS

| | | | |
|---|---|---|---|
| WO | WO-9716835 A1 * | 5/1997 | ............. B03C 1/035 |
| WO | WO-2006/071770 A2 | 7/2006 | |
| WO | WO-2009/005680 A1 | 1/2009 | |
| WO | WO-2012/019765 A1 | 2/2012 | |
| WO | WO-2014/182835 A1 | 11/2014 | |
| WO | WO-2016/137973 A1 | 9/2016 | |
| WO | WO-2018/009766 A1 | 1/2018 | |
| WO | WO-2018/213643 A1 | 11/2018 | |
| WO | WO-2019088106 A1 * | 5/2019 | ............. B03C 1/01 |
| WO | WO-2019/157529 A1 | 8/2019 | |
| WO | WO-2020/123657 A2 | 6/2020 | |
| WO | WO-2021/102043 A1 | 5/2021 | |

OTHER PUBLICATIONS

U.S. Appl. No. 17/332,371, Salmanzadeh et al.
U.S. Appl. No. 17/338,215, filed Salmanzadeh et al.
U.S. Appl. No. 17/851,416, Bharadwaj et al.
U.S. Appl. No. 17/742,793, Alimsijah et al.
U.S. Appl. No. 17/587,861, Shah.
Song et al., "Reactions in Droplets in Microfluidic Channels," available in PMC Jan. 10, 2007, published in final edited form as: Angew Chem Int Ed Engl. 45(44):7336-56 (2006) (Nov. 13, 2006) (58 pages).
Mazutis et al., "Single-cell analysis and sorting using droplet-based microfluidics," available in PMC Aug. 11, 2014, published in final edited form as: Nat Protoc. 8(5):870-91 (2013) (48 pages).
Lennon et al., "A scalable, fully automated process for construction of sequence-ready barcoded libraries for 454," Genome Biol. 11(2):R15 (2010) (9 pages).
"Dynal MPC™-S," Invitrogen, <https://www.veritastk.co.jp/products/pdf/120%2020D.Dynal_MPC-S(rev005).pdf>, dated Oct. 13, 2008, retrieved on Jul. 9, 2019 (1 page).

* cited by examiner

METHODS AND DEVICES FOR MAGNETIC SEPARATION

BACKGROUND OF THE INVENTION

Many biomedical applications rely on high-throughput assays of samples combined with one or more reagents in droplets or particles. For example, in both research and clinical applications, high-throughput genetic tests using target-specific reagents may provide information about samples in drug discovery, biomarker discovery, and clinical diagnostics, among others. Many of these applications, following the formation of a droplet or particle, rely on the presence of a reagent or material within the droplet or particle. For example, some of these applications rely on the presence of a cell, a nucleus, or particulate component thereof. However, before droplet formation, precise sample preparation may be required. Other devices and methods for sorting may disturb a particle and alter its characteristics (e.g., gene expression, activation, or viability). Therefore, improved devices and methods for purification would be beneficial.

SUMMARY OF THE INVENTION

In one aspect, the invention features a device for magnetic separation that includes a housing having a receptacle for a sample holder and a magnetic source. The magnetic source includes at least one sharp feature and is operably connected to the receptacle. For example, the sharp feature may have a corner radius of less than about 10 mm (e.g., less than about 9 mm, 8 mm, 7 mm, 6 mm, 5 mm, 4 mm, 3 mm, 2 mm, or 1 mm, e.g., less than about 990 µm, 980 µm, 970 µm, 960 µm, 950 µm, 940 µm, 930 µm, 920 µm, 910 µm, or 900 µm, e.g., less than about 800 µm, 700 µm, 600 µm, 500 µm, 400 µm, 300 µm, 200 µm, or 100 µm, e.g., less than about 90 µm, 80 µm, 70 µm, 60 µm, or 50 µm, e.g., less than about 45 µm, 40 µm, 35 µm, 30 µm, 25 µm, 20 µm, 15 µm, or 10 µm, e.g., less than about 9 µm, 8 µm, 7 µm, 6 µm, 5 µm, 4 µm, 3 µm, 2 µm or 1 µm, e.g., from about 10 mm to about 1 µm, from about 1 mm to about 1 µm, from about 500 µm to about 1 µm, from about 100 µm to about 1 µm, from about 10 µm to about 1 µm, from about 1 mm to about 10 µm, from about 100 µm to about 10 µm, from about 50 µm to about 10 µm, from about 10 µm to about 1 µm, from about 10 mm to about 1 mm, from about 10 mm to about 5 mm, from about 5 mm to about 500 µm, from about 1 mm to about 500 µm, from about 1 mm to about 10 µm) and/or produce a magnetic gradient of at least about 10 T/m (e.g., at least about 20 T/m, 30 T/m, 40 T/m, 50 T/m, 60 T/m, 70 T/m, 80 T/m, 90 T/m, or 100 T/m, e.g., at least about 200 T/m, 300 T/m, 400 T/m, 500 T/m, 600 T/m, 700 T/m, 800 T/m, 900 T/m, or 1,000 T/m, e.g., at least about 2,000 T/m, 3,000 T/m, 4,000 T/m, 5,000 T/m, 6,000 T/m, 7,000 T/m, 8,000 T/m, 9,000 T/m, 10,000 T/m, e.g., at least about 20,000 T/m, 30,000 T/m, 40,000 T/m, 50,000 T/m, 60,000 T/m, 70,000 T/m, 80,000 T/m, 90,000 T/m, or 100,000 T/m, e.g., at least about 200,000 T/m, 300,000 T/m, 400,000 T/m, 500,000 T/m, 600,000 T/m, 700,000 T/m, 800,000 T/m, 900,000 T/m, or 1,000,000 T/m, e.g., at least about 2,000,000 T/m, 3,000,000 T/m, 4,000,000 T/m, 5,000,000 T/m, 6,000,000 T/m, 7,000,000 T/m, 8,000,000 T/m, 9,000,000 T/m, or 10,000,000, e.g., at least about 100,000,000 T/m, 200,000,000 T/m, 300,000,000 T/m, 400,000,000 T/m, 500,000,000 T/m, 600,000,000 T/m, 700,000,000 T/m, 800,000,000 T/m, 900,000,000 T/m, or 1,000,000,000, or greater, e.g., from about 10 T/m to about 1,000,000,000 T/m, from about 100 T/m to about 1,000,000,000 T/m, from about 1,000 T/m to about 1,000,000,000 T/m, from about 10,000 T/m to about 10,000,000,000 T/m, from about 10,000,000 T/m to about 1,000,000,000 T/m, from about 100,000 T/m, to about 100,000,000 T/m, from about 100,000 T/m to about 100,000,000 T/m, from about 100,000 T/m to about 10,000,000 T/m, from about 10,000,000 T/m to about 100,000,000 T/m). The corner of the sharp feature may be pointed, rounded, or chamfered.

In some embodiments, the magnetic source includes at least two sharp features, e.g., each with a corner radius of less than about 10 mm, e.g., less than about 1 mm and/or producing a magnetic gradient of at least about 10 T/m, e.g., at least about 100 T/m, 1,000 T/m, 10,000 T/m, 100,000 T/m, or 1,000,000 T/m, or 10,000,000 T/m. Each sharp feature may have a corner radius of less than about 10 mm (e.g., less than about 9 mm, 8 mm, 7 mm, 6 mm, 5 mm, 4 mm, 3 mm, 2 mm, or 1 mm, e.g., less than about 990 µm, 980 µm, 970 µm, 960 µm, 950 µm, 940 µm, 930 µm, 920 µm, 910 µm, or 900 µm, e.g., less than about 800 µm, 700 µm, 600 µm, 500 µm, 400 µm, 300 µm, 200 µm, or 100 µm, e.g., less than about 90 µm, 80 µm, 70 µm, 60 µm, or 50 µm, e.g., less than about 45 µm, 40 µm, 35 µm, 30 µm, 25 µm, 20 µm, 15 µm, or 10 µm, e.g., less than about 9 µm, 8 µm, 7 µm, 6 µm, 5 µm, 4 µm, 3 µm, 2 µm or 1 µm, e.g., from about 10 mm to about 1 µm, from about 1 mm to about 1 µm, from about 500 µm to about 1 µm, from about 100 µm to about 1 µm, from about 10 µm to about 1 µm, from about 1 mm to about 10 µm, from about 100 µm to about 10 µm, from about 50 µm to about 10 µm, from about 10 µm to about 1 µm, from about 10 mm to about 1 mm, from about 10 mm to about 5 mm, from about 5 mm to about 500 µm, from about 1 mm to about 500 µm, from about 1 mm to about 10 µm) and/or produce a magnetic gradient of at least about 10 T/m (e.g., at least about 20 T/m, 30 T/m, 40 T/m, 50 T/m, 60 T/m, 70 T/m, 80 T/m, 90 T/m, or 100 T/m, e.g., at least about 200 T/m, 300 T/m, 400 T/m, 500 T/m, 600 T/m, 700 T/m, 800 T/m, 900 T/m, or 1,000 T/m, e.g., at least about 2,000 T/m, 3,000 T/m, 4,000 T/m, 5,000 T/m, 6,000 T/m, 7,000 T/m, 8,000 T/m, 9,000 T/m, 10,000 T/m, e.g., at least about 20,000 T/m, 30,000 T/m, 40,000 T/m, 50,000 T/m, 60,000 T/m, 70,000 T/m, 80,000 T/m, 90,000 T/m, or 100,000 T/m, e.g., at least about 200,000 T/m, 300,000 T/m, 400,000 T/m, 500,000 T/m, 600,000 T/m, 700,000 T/m, 800,000 T/m, 900,000 T/m, or 1,000,000 T/m, e.g., at least about 2,000,000 T/m, 3,000,000 T/m, 4,000,000 T/m, 5,000,000 T/m, 6,000,000 T/m, 7,000,000 T/m, 8,000,000 T/m, 9,000,000 T/m, or 10,000,000, e.g., at least about 100,000,000 T/m, 200,000,000 T/m, 300,000,000 T/m, 400,000,000 T/m, 500,000,000 T/m, 600,000,000 T/m, 700,000,000 T/m, 800,000,000 T/m, 900,000,000 T/m, or 1,000,000,000, or greater, e.g., from about 10 T/m to about 1,000,000,000 T/m, from about 100 T/m to about 1,000,000,000 T/m, from about 1,000 T/m to about 1,000,000,000 T/m, from about 10,000 T/m to about 10,000,000,000 T/m, from about 10,000,000 T/m to about 1,000,000,000 T/m, from about 100,000 T/m, to about 100,000,000 T/m, from about 100,000 T/m to about 100,000,000 T/m, from about 100,000 T/m to about 10,000,000 T/m, from about 10,000,000 T/m to about 100,000,000 T/m).

In some embodiments, the magnetic source surrounds at least 60% (e.g., at least 65%, 70%, 75%, 80%, 85%, 90%, 95%, 99%, or 100%) of the receptacle. In some embodiments, the magnetic source surrounds less than 50% (e.g., less than 45%, 40%, 35%, 30%, 25%, 20%, 15%, 10%, 5%, or less) of the receptacle.

In some embodiments, the sample holder contains a volume of less than about 10,000 µL (e.g., less than about 1,000 µL, less than about 100 µL, or less than about 10 µL, e.g., from about 1 µL to about 10,000 µL, from about 10 µL to about 10,000 µL, from about 100 µL, to about 10,000 µL, from about 1,000 µL to about 10,000 µL, from about 10 µL to about 5,000 µL, from about 10 µL to about 1,000 µL, from about 100 µL to about 1,000 µL, from about 500 µL to about 1,000 µL, from about 1 µL to about 1,000 µL, from about 1 µL to about 500 µL, from about 1 µL to about 100 µL, from about 1 µL to about 50 µL, or from about 1 µL to about 10 µL).

In some embodiments, the device includes a plurality of the magnetic sources.

In some embodiments, the device includes a plurality of the receptacles.

In some embodiments, the magnetic source is removably attached to the housing.

In another aspect, the invention features a method for magnetic separation. The method includes providing the device of any of the above aspects and the sample holder. The sample holder includes a liquid including suspended magnetic particles. The method further includes placing the sample holder in the receptacle, such that the magnetic particles are immobilized at a location in the sample holder.

In some embodiments, the method further includes removing the liquid from the sample holder. Removing the liquid may include, for example, decanting, suctioning, or pipetting the liquid from the sample holder. The method may further include resuspending the magnetic particles in a second liquid. In some embodiments, the steps of removing the liquid and resuspending the magnetic particles may be repeated one or more times.

In another aspect, the invention features device for magnetic separation that includes a vessel having a lumen with an inlet and an outlet and a magnetic source disposed to exert a magnetic field in the lumen.

In some embodiments, the magnetic source surrounds at least 60% (e.g., at least 70%, 80%, 90%, 95%, 97%, 99%, or 100%) of a circumference of the lumen. The magnetic source may be, e.g., a ring.

In some embodiments, the device further includes a filter positioned in the lumen at or upstream of the outlet and configured to trap particles of a predetermined size.

In some embodiments, the filter is disposed at an angle relative to a horizontal cross-section of the lumen. For example, the filter may be disposed at an angle of about 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, or 175° relative to a horizontal cross-section of the lumen.

In some embodiments, the magnetic source is removably attached to the vessel.

In some embodiments, the device further includes a baffle disposed in the lumen at an angle relative to a horizontal cross-section of the lumen. For example, the baffle may be disposed at an angle of about 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, or 175° relative to a horizontal cross-section of the lumen.

The device may further include an outer vessel in which the vessel is disposed. The outer vessel may contain a volume of less than about 10,000 µL.

In some embodiments, the device includes 8, 12, 16, 24, 32, 64, 96, 128, 256, or 396 of the vessels.

In some embodiments, the device includes a plurality of the vessels, each of the vessels disposed within an outer vessel, e.g., a microtiter plate.

The invention further provides a kit comprising a vessel as described herein and an outer vessel as described herein. The vessel may be disposed within the outer vessel.

In another aspect, the invention features a method for magnetic separation using a device as described herein. The method includes providing the device and transporting a liquid including suspended magnetic particles in the lumen so that the magnetic particles are immobilized at a location adjacent the magnetic source. In some embodiments, the vessel is disposed within an outer vessel.

The method may further include removing the liquid from the vessel or outer vessel, e.g., by decanting, suctioning, or pipetting.

The method may further include washing the magnetic particles or particles separated therefrom.

In another aspect, the invention features a kit that includes a vessel having a lumen with an inlet and an outlet; an outer vessel; and a magnetic source disposed to exert a magnetic field in the lumen.

In some embodiments, the vessel is configured to fit within the outer vessel.

In some embodiments, the magnetic source surrounds at least 60% circumference of the lumen.

In some embodiments, the kit further includes a filter positioned in the lumen at or upstream of the outlet and configured to trap particles of a predetermined size.

In some embodiments, the filter is disposed at an angle relative to a horizontal cross-section of the lumen.

In some embodiments, the outer vessel contains a volume of less than about 10,000 µL.

In some embodiments, the kit includes a plurality of the vessels.

In some embodiments, the kit includes 8, 16, 24, 32, 64, 96, or 128, or 396 vessels.

In some embodiments, the magnetic source is removably attached to the vessel.

In some embodiments, the vessel further includes a baffle disposed at an angle relative to a horizontal cross-section of the lumen.

Definitions

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "about," as used herein, refers to ±10% of a recited value.

The terms "adaptor(s)," "adapter(s)," and "tag(s)" may be used synonymously. An adaptor or tag can be coupled to a polynucleotide sequence to be "tagged" by any approach including ligation, hybridization, or other approaches.

The term "barcode," as used herein, generally refers to a label, or identifier, that conveys or is capable of conveying information about an analyte. A barcode can be part of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time.

The term "support," as used herein, generally refers to a particle that is not a biological particle. The particle may be a solid or semi-solid particle. The particle may be a bead, such as a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "biological particle," as used herein, generally refers to a discrete biological system derived from a biological sample. The biological particle may be a virus. The biological particle may be a cell or derivative of a cell. The biological particle may be an organelle from a cell. Examples of an organelle from a cell include, without limitation, a nucleus, endoplasmic reticulum, a ribosome, a Golgi apparatus, an endoplasmic reticulum, a chloroplast, an endocytic vesicle, an exocytic vesicle, a vacuole, and a lysosome. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell but may not include other constituents of the cell. An example of such constituents is a nucleus or another organelle of a cell. A cell may be a live cell. The live cell may be capable of being cultured, for example, being cultured when enclosed in a gel or polymer matrix or cultured when comprising a gel or polymer matrix.

The term "fluidically connected," as used herein, refers to a direct connection between at least two device elements, e.g., a channel, reservoir, etc., that allows for fluid to move between such device elements without passing through an intervening element.

The term "genome," as used herein, generally refers to genomic information from a subject, which may be, for example, at least a portion or an entirety of a subject's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together may constitute a human genome.

The term "in fluid communication with", as used herein, refers to a connection between at least two device elements, e.g., a channel, reservoir, etc., that allows for fluid to move between such device elements with or without passing through one or more intervening device elements.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA or a DNA molecule. The macromolecular constituent may comprise RNA or an RNA molecule. The RNA may be coding or non-coding. The RNA may be messenger RNA (mRNA), ribosomal RNA (rRNA) or transfer RNA (tRNA), for example. The RNA may be a transcript. The RNA molecule may be (i) a clustered regularly interspaced short palindromic (CRISPR) RNA molecule (crRNA) or (ii) a single guide RNA (sgRNA) molecule. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide or a protein. The polypeptide or protein may be an extracellular or an intracellular polypeptide or protein. The macromolecular constituent may also comprise a metabolite. These and other suitable macromolecular constituents (also referred to as analytes) will be appreciated by those skilled in the art (see U.S. Pat. Nos. 10,011,872 and 10,323,278, and PCT Publication No. WO 2019/157529, each of which is incorporated herein by reference in its entirety).

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise an oligonucleotide or polypeptide sequence. The molecular tag may comprise a DNA aptamer. The molecular tag may be or comprise a primer. The molecular tag may be or comprise a protein. The molecular tag may comprise a polypeptide. The molecular tag may be a barcode.

The term "oil," as used herein, generally refers to a liquid that is not miscible with water. An oil may have a density higher or lower than water and/or a viscosity higher or lower than water.

The term "particulate component of a cell" refers to a discrete biological system derived from a cell or fragment thereof and having at least one dimension of 0.01 µm (e.g., at least 0.01 µm, at least 0.1 µm, at least 1 µm, at least 10 µm, or at least 100 µm). A particulate component of a cell may be, for example, an organelle, such as a nucleus, an exosome, a liposome, an endoplasmic reticulum (e.g., rough or smooth), a ribosome, a Golgi apparatus, a chloroplast, an endocytic vesicle, an exocytic vesicle, a vacuole, a lysosome, or a mitochondrion.

The term "sample," as used herein, generally refers to a biological sample of a subject. The biological sample may be a nucleic acid sample or protein sample. The biological sample may be derived from another sample. The sample may be a tissue sample, such as a biopsy, core biopsy, needle aspirate, or fine needle aspirate. The sample may be a liquid sample, such as a blood sample, urine sample, or saliva sample. The sample may be a skin sample. The sample may be a cheek swap. The sample may be a plasma or serum sample. The sample may include a biological particle, e.g., a cell, a nucleus, or virus, or a population thereof, or it may alternatively be free of biological particles. A cell-free sample may include polynucleotides. Polynucleotides may be isolated from a bodily sample that may be selected from the group consisting of blood, plasma, serum, urine, saliva, mucosal excretions, sputum, stool, and tears.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by ILLUMINA®, Pacific Biosciences (PACBIO®), Oxford NANOPORE®, or Life Technologies (ION TORRENT®). Alternatively or in addition, sequencing may be performed using nucleic acid amplification, polymerase chain reaction (PCR) (e.g., digital PCR, quantitative PCR, or real time PCR), or isothermal amplification. Such devices may provide a plurality of raw genetic data corresponding to the genetic information of a subject (e.g., human), as generated by the device from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "sorter," as used herein, generally refers to a mechanism that causes movement of one or more droplets or particles into one of two or more partitions (e.g., channels or regions), e.g., in a collection region. A sorter may be active or passive. In active sorting, actuation of the sorter moves a droplet to a partition. In passive sorting, droplets are moved to a partition based on an intrinsic property, e.g., mass, buoyancy, size, magnetic properties, or electrical properties.

The term "subject," as used herein, generally refers to an animal, such as a mammal (e.g., human) or avian (e.g., bird), or other organism, such as a plant. The subject can be a vertebrate, a mammal, a mouse, a primate, a simian or a human. Animals may include, but are not limited to, farm animals, sport animals, and pets. A subject can be a healthy or asymptomatic individual, an individual that has or is suspected of having a disease (e.g., cancer) or a predisposition to the disease, or an individual that is in need of therapy or suspected of needing therapy. A subject can be a patient.

The term "substantially stationary," as used herein with respect to droplet or particle formation, generally refers to a state when motion of formed droplets or particles in the continuous phase is passive, e.g., resulting from the difference in density between the dispersed phase and the continuous phase.

BRIEF DESCRIPTION OF THE DRAWINGS

FIG. 2A shows a top view and FIG. 2B shows a side view. The magnetic particles are shown clustered near the sharp features of the magnet, whereas the unlabeled particles (and/or extracellular molecules, e.g., RNA — depicted as V-shaped symbols) do not cluster near the sharp features of the magnet.

DETAILED DESCRIPTION OF THE INVENTION

Figure 1:
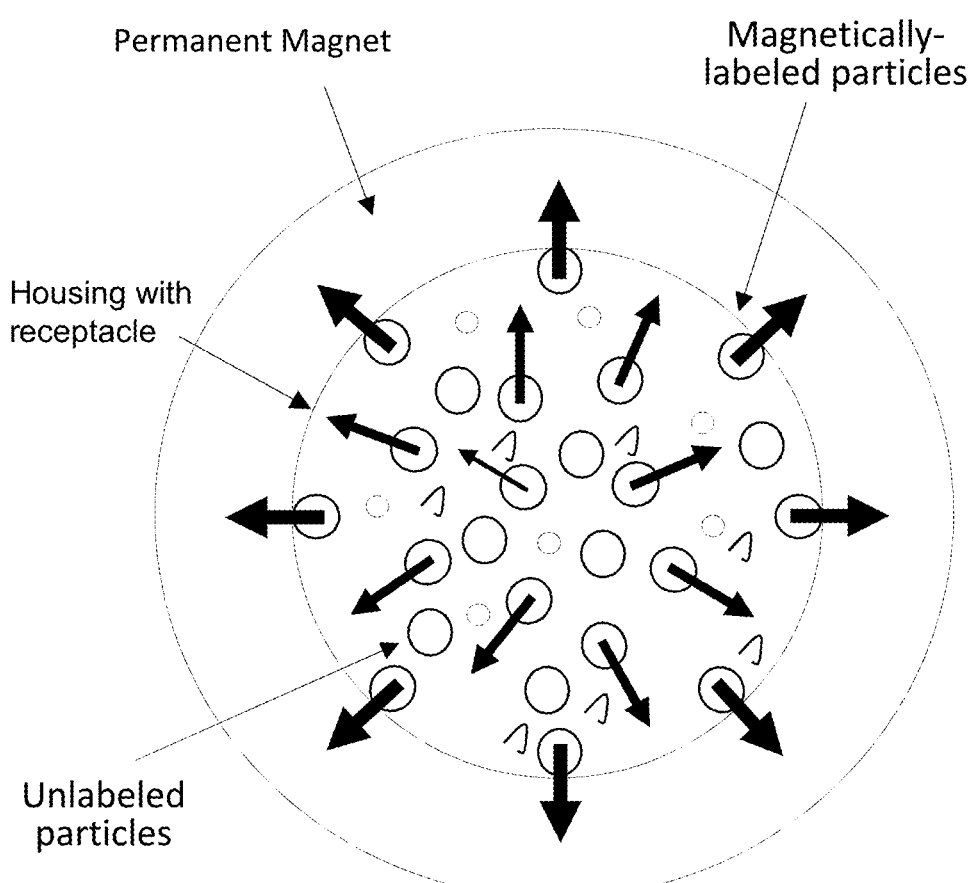
FIG. 1 is a schematic drawing of a device that includes a permanent magnet that surrounds a sample holder containing a liquid with a mixture of magnetically labelled and unlabeled particles. The magnetically labelled particles are attracted by the magnet and move towards the edge of the sample holder, whereas the unlabeled particles are not attracted and do not move towards to the edge of the sample holder. In addition, background or extracellular molecules, e.g., RNA (depicted as v-shaped symbols), are unlabeled and not attracted to the magnet.

The invention provides devices, kits, and systems for magnetic separation of particles and methods of their use. The devices may be used to sort particles of a desired property, e.g., for genetic sequencing.

The devices, systems, and methods described herein allow for the separation of magnetic particles. The magnetic particles may be released from a droplet or larger particle or may be a label present on another particle (e.g., a cell, a nucleus, a macromolecular constituent of a cell, a gel bead, or a combination thereof). The magnetic particles may be used to purify particles attached thereto for incorporation into droplets or other, larger particles (e.g., gels).

In one embodiment of the invention, the magnetic separation is performed by a magnetic separation device that includes one or more magnetic sources with a sharp feature that provides a magnetic force to separate magnetic particles from non-magnetic particles. In another embodiment of the invention, the magnetic separation is performed by a magnetic separation device that includes a vessel having a lumen with an inlet and an outlet and a magnetic source disposed to exert a magnetic field in the lumen. Advantages of the devices and methods described herein are that the magnetic separation devices provide a quick and gentle separation that minimizes damage to the magnetic particles or the components attached thereto, e.g., cell disruption or changes in gene expression, which may increase viability of the component being separated (e.g., a cell, a nucleus, or a macromolecular constituent thereof, e.g., organelle), e.g., relative to other devices and methods. Furthermore, the devices and methods described herein can be used with very small sample volumes (e.g., less than 100 µL) in which high recovery yield is critical.

Magnetic Separation Device

One embodiment of a device for magnetic separation includes a housing that has a receptacle for a sample holder. The device includes a magnetic source that is operably connected to the receptacle. For example, the magnetic source may be positioned to substantially surround the sample holder. By positioning the magnetic source outside of the sample holder, the magnetic source does not directly contact the magnetic particles. Therefore, when the magnetic particles are attached to, e.g., a biological particle (e.g., a cell, a nucleus or macromolecular constituent thereof), the magnetic particles do not become entrapped, e.g., as may occur in a column packed with magnetic beads or magnetic sources, and the magnetic particles may be more easily released. Additionally, this arrangement allows the device to be reused with multiple samples as the magnetic source does not become contaminated between uses and, therefore, does not require washing or sterilization for subsequent use. The components of the device are described in more detail below.

Housing

The housing of the magnetic separation device may be or include any geometric structure suitable to contain a receptacle for a sample holder. The housing may include a plurality (e.g., 2, 3, 4, 5, 6, 7, 8, 9, 10, 11, 12, 16, 24, 32, 64, 96, or more) of receptacles. For example, the housing may include a linear array of receptacles configured to receive a plurality of, e.g., 8, 12, 16, 24, or more, sample holders, e.g., microcentrifuge or PCR tubes, e.g., in a strip. The receptacles may be round, square, or any geometric shape that mates with or matches the size and shape of the sample holder. The housing may be fabricated of any suitable material, such as a rigid or semi-rigid polymer. The housing may contain a flat surface to allow it to lay stationary. The housing may be configured to be manually manipulated by a user or manipulated by an automated device, such as a robot.

Magnetic Source

The magnetic source is any source that provides a magnetic field that exerts force on magnetic particles. A magnetic field may be provided by one or more magnetic sources such as, e.g., one or more magnets, such as permanent magnet or an electromagnet. In one embodiment, the magnetic source includes at least one (e.g., at least 2, 3, 4, 5, 6, 7, 8, 9, 10, or more) sharp feature. The corner of the sharp feature may be, for example, pointed, rounded, or chamfered. For example, the sharp feature may have a corner radius of less than about 10 mm (e.g., less than about 9 mm, 8 mm, 7 mm, 6 mm, 5 mm, 4 mm, 3 mm, 2 mm, or 1 mm, e.g., less than about 990 µm, 980 µm, 970 µm, 960 µm, 950 µm, 940 µm, 930 µm, 920 µm, 910 µm, or 900 µm, e.g., less than about 800 µm, 700 µm, 600 µm, 500 µm, 400 µm, 300 µm, 200 µm, or 100 µm, e.g., less than about 90 µm, 80 µm, 70 µm, 60 µm, or 50 µm, e.g., less than about 45 µm, 40 µm, 35 µm, 30 µm, 25 µm, 20 µm, 15 µm, or 10 µm, e.g., less than about 9 µm, 8 µm, 7 µm, 6 µm, 5 µm, 4 µm, 3 µm, 2 µm or 1 µm, e.g., from about 10 mm to about 1 µm, from about 1 mm to about 1 µm, from about 500 µm to about 1 µm, from about 100 µm to about 1 µm, from about 10 µm to about 1 µm, from about 1 mm to about 10 µm, from about 100 µm to about 10 µm, from about 50 µm to about 10 µm, from about 10 µm to about 1 µm, from about 10 mm to about 1 mm, from about 10 mm to about 5 mm, from about 5 mm to about 500 µm, from about 1 mm to about 500 µm, from about 1 mm to about 10 µm). For example, the feature may have a corner radius of less than about 1 mm. The magnetic source may produce a magnetic gradient of at least about 10 T/m (e.g., at least about 20 T/m, 30 T/m, 40 T/m, 50 T/m, 60 T/m, 70 T/m, 80 T/m, 90 T/m, or 100 T/m, e.g., at least about 200 T/m, 300 T/m, 400 T/m, 500 T/m, 600 T/m, 700 T/m, 800 T/m, 900 T/m, or 1,000 T/m, e.g., at least about 2,000 T/m, 3,000 T/m, 4,000 T/m, 5,000 T/m, 6,000 T/m, 7,000 T/m, 8,000 T/m, 9,000 T/m, 10,000 T/m, e.g., at least about 20,000 T/m, 30,000 T/m, 40,000 T/m, 50,000 T/m, 60,000 T/m, 70,000 T/m, 80,000 T/m, 90,000 T/m, or 100,000 T/m, e.g., at least about 200,000 T/m, 300,000 T/m, 400,000 T/m, 500,000 T/m, 600,000 T/m, 700,000 T/m, 800,000 T/m, 900,000 T/m, or 1,000,000 T/m, e.g., at least about 2,000,000 T/m, 3,000,000 T/m, 4,000,000 T/m, 5,000,000 T/m, 6,000,000 T/m, 7,000,000 T/m, 8,000,000 T/m, 9,000,000 T/m, or 10,000,000, e.g., at least about 100,000,000 T/m, 200,000,000 T/m, 300,000,000 T/m, 400,000,000 T/m, 500,000,000 T/m, 600,000,000 T/m, 700,000,000 T/m, 800,000,000 T/m, 900,000,000 T/m, or 1,000,000,000, or greater, e.g., from about 10 T/m to about 1,000,000,000 T/m, from about 100 T/m to about 1,000,000,000 T/m, from about 1,000 T/m to about 1,000,000,000 T/m, from about 10,000 T/m to about 10,000,000,000 T/m, from about 10,000,000 T/m to about 1,000,000,000 T/m, from about 100,000 T/m, to about 100,000,000 T/m, from about 100,000 T/m to about 100,000,000 T/m, from about 100,000 T/m to about 10,000,000 T/m, from about 10,000,000 T/m to about 100,000,000 T/m. For example, the sharp feature may produce a magnetic gradient of at least about 100,000 T/m.

The sharp feature of the magnetic source allows the magnetic source to produce a magnetic field gradient, e.g., that is stronger compared to a magnetic source without a sharp feature, e.g., having a corner radius of less than 10 mm, e.g., less than 1 mm. The magnetic source may have a polygonal shape. For example, a cross-section of the magnetic source may be a polygon with 3, 4, 5, 6, 7, 8, 9, 10, 11, 12, or more sides. The vertices of the polygon may have a corner radius of less than about 10 mm, e.g., less than about 1 mm, or produce a magnetic gradient of at least about 10 T/m, e.g., at least about 100,000 T/m. The device may include a magnetic source with a plurality of sharp features or a plurality of magnetic sources, each having a sharp feature.

One of skill in the art would appreciate that the values above, such as the corner radius of the feature or the magnetic gradient, may be determined empirically. For example, the magnetic gradient may depend on factors, such as the size of magnetic particles (e.g., that are being separated, e.g., that are attached to a biological particle or macromolecular constituent thereof), the number of magnetic particles attached to each biological particle or macromolecular constituent thereof, the size and material of the magnetic particles, the tolerance of fabricating the magnets and the receptacle or sample holder, the tightness of fit between the sample holder and the receptacle, the thickness of the housing or the sample holder, and the sharpness (angle) of the feature.

The magnetic source is positioned on, within, or near the housing such that is operatively connected to a receptacle configured to receive the sample holder. The magnetic source may be part of the device, e.g., integrated within the housing. Alternatively, the magnetic source may be removably attached to the device (e.g., the housing). The magnetic source may be positioned to substantially surround the receptacle, e.g., in an annular or incomplete ring-like configuration around the receptable, e.g., at least 50%, e.g., at least, 60%, 65%, 70%, 75%, 80%, 85%, 90%, 95%, 99%, or 100% of the perimeter. Alternatively, the magnetic source may only surround a portion (e.g., less than 50%, 45%, 40%, 35%, 30%, 25%, 20%, 15%, 10%, 5%, or less) of the receptacle. The device may include a plurality (e.g., 2, 3, 4, 5, 6, 7, 8, 9, 10, or more) of magnetic sources positioned such that each magnetic source is operatively connected to the receptacle. The magnetic sources may be clustered near one region, e.g., in a band at one vertical position of the receptacle or may be dispersed over the surface of the receptacle.

Sample Holder

The sample holder may be any suitable geometry, such as a well, channel, reservoir, tube, or portion thereof, and the like. The sample holder may be, for example, a microcentrifuge tube or a PCR tube. The sample holder may have a volume of less than about 10,000 µL (e.g., less than about 1,000 µL, less than about 100 µL, or less than about 10 µL, e.g., from about 1 µL, to about 10,000 µL, from about 10 µL to about 10,000 µL, from about 100 µL, to about 10,000 µL, from about 1,000 µL, to about 10,000 µL, from about 10 µL, to about 5,000 µL, from about 10 µL, to about 1,000 µL, from about 100 µL, to about 1,000 µL, from about 500 µL, to about 1,000 µL, from about 1 µL, to about 1,000 µL, from about 1 µL, to about 500 µL, from about 1 µL, to about 100 µL, from about 1 µL, to about 50 µL, or from about 1 µL, to about 10 µL).

The sample holder may have a thickness of from about 10 µm to about 10 mm (e.g., from about 10 µm to about 1 mm, from about 10 µm to about 100 µm, from about 50 µm to about 100 µm, from about 100 µm to about 10 mm, from about 1 mm to about 10 mm, from about 500 µm to about 1 mm, from about 1 mm to about 5 mm, from about 1 mm to about 2 mm, e.g., about 1.5 mm). In some embodiments, the sample holder may have thickness of from about 10 µm to about 100 µm, e.g., about 10 µm, 20 µm, 30 µm, 40 µm, 50 µm, 60 µm, 70 µm, 80 µm, 90 µm, or 100 µm, e.g., from about 100 µm to about 1000 µm, e.g., about 200 µm, 300 µm, 400 µm, 500 µm, 600 µm, 700 µm, 800 µm, 900 µm, or 1000 µm, e.g., from about 1 mm to about 10 mm, e.g., 2 mm, 3 mm, 4 mm, 5 mm, 6 mm, 7 mm, 8 mm, 9 mm, or 10 mm.

Magnetic Separation Device with a Lumen

Another embodiment of a magnetic separation as described herein includes a vessel having a lumen with an inlet and an outlet and a magnetic source disposed to exert a magnetic field in the lumen. The vessel may be disposed within an outer vessel. The magnetic source may be disposed to surround at least 60% (e.g., at least 70%, 80%, 90%, 95%, 97%, 99%, or 100%) of a circumference of the lumen. The magnetic source may be removably attached to the vessel. The magnetic source is positioned to attract magnetic particles in the vessel such that they are separated from the remainder of a sample as it passes the magnetic source. The magnetic source is any that provides a magnetic field that exerts force on magnetic particles. A magnetic field may be provided by one or more magnetic sources such as, e.g., one or more magnets, such as permanent magnet or an electromagnet. The magnetic source may be, e.g., a magnetic ring.

The vessel may have any suitable geometry, such as a tube. The vessel may be substantially cylindrical or conical. The vessel may have a cap (e.g., removable cap). The vessel may have a volume of less than about 10,000 µL, (e.g., less than about 1,000 µL, less than about 100 µL, or less than about 10 µL, e.g., from about 1 µL, to about 10,000 µL, from about 10 µL, to about 10,000 µL, from about 100 µL, to about 10,000 µL, from about 1,000 µL, to about 10,000 µL, from about 10 µL, to about 5,000 µL, from about 10 µL, to about 1,000 µL, from about 100 µL, to about 1,000 µL, from about 500 µL, to about 1,000 µL, from about 1 µL, to about 1,000 µL, from about 1 µL, to about 500 µL, from about 1 µL, to about 100 µL, from about 1 µL, to about 50 µL, or from about 1 µL, to about 10 µL).

The vessel may have a thickness of from about 10 µm to about 10 mm (e.g., from about 10 µm to about 1 mm, from about 10 µm to about 100 µm, from about 50 µm to about 100 µm, from about 100 µm to about 10 mm, from about 1 mm to about 10 mm, from about 500 µm to about 1 mm, from about 1 mm to about 5 mm, from about 1 mm to about 2 mm, e.g., about 1.5 mm). In some embodiments, the vessel may have thickness of from about 10 µm to about 100 µm, e.g., about 10 µm, 20 µm, 30 µm, 40 µm, 50 µm, 60 µm, 70 µm, 80 µm, 90 µm, or 100 µm, e.g., from about 100 µm to about 1000 µm, e.g., about 200 µm, 300 µm, 400 µm, 500 µm, 600 µm, 700 µm, 800 µm, 900 µm, or 1000 µm, e.g., from about 1 mm to about 10 mm, e.g., 2 mm, 3 mm, 4 mm, 5 mm, 6 mm, 7 mm, 8 mm, 9 mm, or 10 mm.

The vessel may be configured as an insert for an outer vessel, such as a microcentrifuge tube or a PCR tube. The outer vessel can have any suitable geometry, such as tube or microtiter plate. The outer vessel may be substantially cylindrical or conical. The outer vessel may have a cap (e.g., removable cap). The outer vessel may have a volume of less than about 10,000 µL, (e.g., less than about 1,000 µL, less than about 100 µL, or less than about 10 µL, e.g., from about 1 µL, to about 10,000 µL, from about 10 µL, to about 10,000 µL, from about 100 µL, to about 10,000 µL, from about 1,000 µL, to about 10,000 µL, from about 10 µL, to about 5,000 µL, from about 10 µL, to about 1,000 µL, from about 100 µL, to about 1,000 µL, from about 500 µL, to about 1,000 µL, from about 1 µL, to about 1,000 µL, from about 1 µL, to about 500 µL, from about 1 µL, to about 100 µL, from about 1 µL, to about 50 µL, or from about 1 µL, to about 10 µL).

The outer vessel may have a thickness of from about 10 µm to about 10 mm (e.g., from about 10 µm to about 1 mm, from about 10 µm to about 100 µm, from about 50 µm to about 100 µm, from about 100 µm to about 10 mm, from about 1 mm to about 10 mm, from about 500 µm to about 1 mm, from about 1 mm to about 5 mm, from about 1 mm to about 2 mm, e.g., about 1.5 mm). In some embodiments, the outer vessel may have thickness of from about 10 μm to about 100 μm, e.g., about 10 μm, 20 μm, 30 μm, 40 μm, 50 μm, 60 μm, 70 μm, 80 μm, 90 μm, or 100 μm, e.g., from about 100 μm to about 1000 μm, e.g., about 200 μm, 300 μm, 400 μm, 500 μm, 600 μm, 700 μm, 800 μm, 900 μm, or 1000 μm, e.g., from about 1 mm to about 10 mm, e.g., 2 mm, 3 mm, 4 mm, 5 mm, 6 mm, 7 mm, 8 mm, 9 mm, or 10 mm.

A plurality of vessels may be employed together. Each of the vessels may be configured to fit within an outer vessel, e.g., a well in a microtiter plate. A single outer vessel may be employed with multiple devices of the invention. For example, 8, 12, 16, 24, 32, 64, 96, 128, 256, or 396 of the vessels may be employed with 1, 8, 12, 16, 24, 32, 64, 96, 128, 256, or 396 of the outer vessels.

In some embodiments, the device includes a filter positioned in the lumen at or upstream of the outlet and configured to trap particles (e.g., biological particles, e.g., cells or nuclei) of a predetermined size. The filter may be disposed at an angle relative to a horizontal cross-section of the lumen. For example, the filter may be disposed at an angle of about 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, or 175° relative to a horizontal cross-section of the lumen.

In some embodiments, the device includes a baffle positioned in the lumen upstream of the outlet, e.g., to direct fluid or particles in a desired direction in the lumen. The baffle may be disposed at an angle relative to a horizontal cross-section of the lumen. For example, the baffle may be disposed at an angle of about 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, or 175° relative to a horizontal cross-section of the lumen. A baffle may be positioned at a different angle than a filter.

The lumen may be of any suitable cross section to allow the sample to pass, e.g., circular. The cross section of the lumen need not be constant. In some embodiments, the lumen may have a cross section dimension of between 1 μm and 10 mm, e.g., between 100 μm and 5 mm.

The vessel may also include a valve or seal to hold sample liquid until a desired condition is met, e.g., a certain force is reached in a centrifuge. A valve may be passive or active. Passive valves may include a narrowing of the lumen or a change in surface properties, e.g., to more hydrophobic for an aqueous sample. Seals include frangible seals that rupture at a predetermined force.

In some embodiments, the vessel includes a reservoir, e.g., to hold fluids and particles passing through the outlet. Access to the reservoir may be a valve or seal or by cutting or piercing the vessel.

Sample

The samples that may be used with the devices described herein may be any liquid, e.g., an aqueous or non-aqueous liquid, that contains suspended magnetic particles. The magnetic particles may be attached to other particles, e.g., biological particles, e.g., a cell, a nucleus, or a macromolecular constituent thereof, e.g., an organelle or nucleic acid, or otherwise soluble substances, e.g., proteins, nucleic acids, etc. including extracellular molecules or analytes.

In some instances, unwanted molecules or analytes in a sample containing cells may be extracellular molecules or analytes. Extracellular analytes may be chemical, biological, or biochemical molecules or particles that are outside of a cell. The extracellular analytes may include any kind of molecules, such as nucleic acid molecules, peptides, proteins, substrates, a sequence of nucleic acids, a sequence of amino acids, or other kinds of molecules. Extracellular molecules may include extracellular nucleic acid molecules such as DNA and/or RNA or any other types of nucleic acid molecules and/or any combination thereof that are not inside a cell or cell nucleus. In some cases, extracellular molecules may be impurities in the sample. Additional disclosure regarding unwanted extracellular analytes is provided in U.S. Provisional Patent Application No. 63/109,972, which is incorporated here by reference in its entirety.

Extracellular molecules (e.g., extracellular nucleic acid molecules) may also be referred to as free-floating molecules (e.g., free-floating nucleic acid molecules), ambient molecules (e.g., ambient nucleic acid molecules), and/or background molecules (e.g., background nucleic acid molecules). Extracellular molecules may include molecules in a sample that are not inside a cell or cell nucleus which may act as impurities and may interfere with the quality of data obtained from analyzing the cells or cell nuclei of the sample. In some cases, extracellular molecules may be present without interfering with the quality of data obtained from analyzing the cells or cell nuclei of the sample.

In some instances, the extracellular molecules may include molecules such as extracellular peptides, proteins, substrates, a sequence of amino acids, chemicals, impurities and/or any combination thereof. For example, a sample with a cell or cell nucleus may further include extracellular molecules such as proteins and/or peptides.

In some instances, the extracellular molecules may include or be extracellular nucleic acid molecules. The extracellular nucleic acid molecules may include ribonucleic acid (RNA) or deoxyribonucleic acid (DNA). In some examples, extracellular nucleic acid may include at least one of messenger RNA (mRNA), chromosome, and genomic DNA (gDNA). In some examples, the extracellular nucleic acid molecules may have a size of at least about 5 base pairs (bp) or nucleotides (nt), for example, at least about 5 by or nt, 10 by or nt, 15 by or nt, 20 by or nt, 25 by or nt, 30 by or nt, 35 by or nt, 40 by or nt 50 bp or nt, 60 bp or nt, 70 bp or nt, 80 bp or nt, 90 bp or nt, 100 bp or nt, 200 bp or nt, 300 bp or nt, 400 bp or nt, 500 bp or nt, 600 bp or nt, 700 bp or nt, 800 bp or nt, 900 bp or nt, 1 kbp or knt, or larger in size. In some instances, extracellular nucleic acid molecules may be equal to or smaller than about: 500 bp or nt, 400 bp or nt, 300 bp or nt, 200 bp or nt, 100 bp or nt, 50 bp or nt, 40 bp or nt, 30 bp or nt, 20 bp or nt, 10 bp or nt, 5 bp or nt, or smaller, for example smaller than 50 bp or nt.

Extracellular analytes (e.g., extracellular nucleic acid molecules) may have been released in the sample from a cell or cell nucleus, for example, as a result of processing, treating, and/or manipulating a sample including a cell and/or a cell nucleus (e.g., during sample preparation). Such processing may have caused cell lysis or a loss of the integrity of the cell membrane and/or the nuclear membrane. This phenomenon may occur in any kind of cell, such as any cell type listed elsewhere herein or other types of cells. In some cases, a cell type that is more fragile may be more prone to getting lysed during sample preparation. Such cell type may be more likely to release extracellular molecules in the sample. Alternatively, the extracellular molecules (e.g., extracellular nucleic acid molecules) may have other origins and/or causes. Recognized is a need to address a contamination (or cross-contamination) of a sample with extracellular molecules (e.g., extracellular nucleic acid molecules) and their interference with data analysis (e.g., single cell analysis such as single cell sequencing or other sample processing and analysis techniques or procedures).

In some instances, the presence of extracellular molecules (e.g., extracellular nucleic acid molecules) in a sample including cells and/or cell nuclei may adversely affect and/or at least to some extent compromise the precision or quality of the results of the analysis (e.g., single cell analysis and/or data clustering results). For example, the goal may be to analyze the nucleic acid molecules in the cells and/or cell nuclei (e.g., intracellular nucleic acid molecules) of the sample. The method may further include clustering the data generated for the cells and/or the cell nuclei of the sample into more than one subpopulation (e.g., cluster the cell into multiple subpopulations). The method may further include identifying combinations of characteristics and/or parameters (e.g., markers) that may provide important information regarding each subpopulation and/or define the subpopulation in terms of a given state or condition of the sample or the subject, for example a disease marker or a diagnosis of the subject. The presence of extracellular molecules such as extracellular nucleic acid molecules may interfere with such clustering and/or identification in one or more ways. This phenomenon may also be referred to as cross-contamination. For example, the presence of extracellular molecules (e.g., ambient or background molecules such as nucleic acid molecules) may cause two or more subpopulations to blend together and the data (e.g., signal or sequencing reads) relating to a cell, cell nucleus, and/or the intracellular nucleic acid molecules thereof to be detected or categorized across two or more subpopulations. Extracellular molecules (e.g., extracellular nucleic acid molecules) may cause artifacts and/or noise in the data, alter the number of subpopulations resulted from the cluster analysis, interfere with the data in other ways, and/or any combinations thereof. This may cause imprecision in data and may adversely affect interpretation of results and/or decision making based on such data and/or data clustering. Therefore, depending on the application, there may be a need to ascertain the composition of a sample prior to use in, for example, single cell processing, including partitioning.

In some instances, the extracellular molecules (e.g., extracellular nucleic acid molecules), such as nucleic acid molecules inside a sample that are external to a cell or cell nucleus may generate information, such as signals (e.g., sequence reads) during sample processing and/or analysis. For example, a sample including a cell or cell nucleus which also includes extracellular nucleic acid molecules may be subjected to processing and analysis, for example, single cell sequencing (e.g., single cell RNA sequencing). In such case, the signals obtained from the extracellular nucleic acid molecules may be considered noise and may contaminate the data obtained from the intracellular nucleic acid molecules or data obtained from the nucleic acid molecules inside the cell nuclei. In this example, digesting or otherwise decreasing or removing the extracellular nucleic acid molecules from the sample (e.g., prior to sequencing) may enhance the quality of the single cell sequencing data and a clustering thereof.

In some instances, reduced amounts of extracellular molecules (e.g., extracellular nucleic acid molecules) or an absence thereof in the composition (e.g., processed sample) may result in more precise and/or more informative data with reduced noise, artifacts, imprecision, and/or error. Such data may include higher quality and may result in improved interpretation of results and/or more informed decision making. In some cases, the elimination of extracellular molecules (e.g., extracellular nucleic acid molecules) may reduce the time and expense of data analysis, for example, by providing cleaner data with reduced noise.

The devices described herein are particularly advantageous for small volumes of sample (e.g., less than 100 µL, 90 µL, 80 µL, 70 µL, 60 µL, 50 µL, 40 µL, 30 µL, 20 µL, 10 µL, 9 µL, 8 µL, 7 µL, 6 µL, 5 µL, 4 µL, 3 µL, 2 µL, or 1 µL), or volumes of samples that contain a low number of magnetic particles (e.g., that are attached to a desired biological particle, e.g., a cell, a nucleus, or macromolecular constituent thereof). For example, the sample holder may contain a sample with fewer than 1,000, e.g., less than 900, 800, 700, 600, 500, 400, 300, 200, or 100, magnetic particles.

The samples may be used for preparation before incorporation into droplets. Alternatively, the samples may be derived from droplets, e.g., following breaking or destabilization of droplets. Droplets generally refer to one liquid suspended in a second immiscible liquid and may be formed in which one or more magnetic particles are encapsulated within the droplet.

In general, droplets may be formed by shaking or stirring a liquid to form individual droplets, creating a suspension or an emulsion containing individual droplets, or forming the droplets through pipetting techniques, e.g., with needles, or the like. The droplets may be formed made using a micro-, or nanofluidic droplet maker. Examples of such droplet makers include, e.g., a T-junction droplet maker, a Y-junction droplet maker, a channel-within-a-channel junction droplet maker, a cross (or "X") junction droplet maker, a flow-focusing junction droplet maker, a micro-capillary droplet maker (e.g., co-flow or flow-focus), and a three-dimensional droplet maker. The droplets may be produced using a flow-focusing device, or with emulsification systems, such as homogenization, membrane emulsification, shear cell emulsification, and fluidic emulsification. Droplets may also be formed as described in WO 2019/040637.

Discrete liquid droplets may be encapsulated by a carrier fluid that wets the microchannel. These droplets, sometimes known as plugs, form the dispersed phase in which the reactions occur. Systems that use plugs differ from segmented-flow injection analysis in that reagents in plugs do not come into contact with the microchannel. In T junctions, the disperse phase and the continuous phase are injected from two branches of the "T". Droplets of the disperse phase are produced as a result of the shear force and interfacial tension at the fluid—fluid interface. The phase that has lower interfacial tension with the channel wall is the continuous phase. To generate droplets in a flow-focusing configuration, the continuous phase is injected through two outside channels and the disperse phase is injected through a central channel into a narrow orifice. Other geometric designs to create droplets would be known to one of skill in the art. Methods of producing droplets are disclosed in Song et al. *Angew. Chem.* 45: 7336-7356, 2006, Mazutis et al. *Nat. Protoc.* 8(5):870-891, 2013, U.S. Pat. No. 9,839,911; U.S. Pub. Nos. 2005/0172476, 2006/0163385, and 2007/0003442, PCT Pub. Nos. WO 2009/005680 and WO 2018/009766. In some embodiments, electric fields or acoustic waves may be used to produce droplets, e.g., as described in PCT Pub. No. WO 2018/009766.

Surface Properties

A surface of the device may include a material, coating, or surface texture that determines the physical properties of the device. In particular, the flow of liquids through a device of the invention may be controlled by the device surface properties (e.g., wettability of a liquid-contacting surface). In some cases, a device portion (e.g., a channel or sorter) may have a surface having a wettability suitable for facilitating liquid flow (e.g., in a channel) or assisting droplet formation of a first liquid in a second liquid (e.g., in a channel), e.g., if droplet formation is performed.

Wetting, which is the ability of a liquid to maintain contact with a solid surface, may be measured as a function of a water contact angle. A water contact angle of a material can be measured by any suitable method known in the art, such as the static sessile drop method, pendant drop method, dynamic sessile drop method, dynamic Wilhelmy method, single-fiber Wilhelmy method, single-fiber meniscus method, and Washburn's equation capillary rise method. The wettability of each surface may be suited to separating magnetic particles, e.g., coupled to cells, nuclei, or particulate components thereof.

For example, portions of the device carrying aqueous phases (e.g., a channel) may have a surface material or coating that is hydrophilic or more hydrophilic than other portions of the device, e.g., include a material or coating having a water contact angle of less than or equal to about 90°, and/or other portions of the device around the channel may have a surface material or coating that is hydrophobic or more hydrophobic than the channel, e.g., include a material or coating having a water contact angle of greater than 70° (e.g., greater than 90°, greater than 95°, greater than 100° (e.g., 95°-120° or 100°-10°)). In certain embodiments, a portion of the device may include a material or surface coating that reduces or prevents wetting by aqueous phases. The device can be designed to have a single type of material or coating throughout. Alternatively, the device may have separate regions having different materials or coatings.

The device surface properties may be those of a native surface (i.e., the surface properties of the bulk material used for the device fabrication) or of a surface treatment. Non-limiting examples of surface treatments include, e.g., surface coatings and surface textures. In one approach, the device surface properties are attributable to one or more surface coatings present in a device portion. Hydrophobic coatings may include fluoropolymers (e.g., AQUAPEL® glass treatment), silanes, siloxanes, silicones, or other coatings known in the art. Other coatings include those vapor deposited from a precursor such as henicosyl-1,1,2,2-tetrahydrododecyldimethyltris(dimethylaminosilane); hen icosyl-1,1,2,2-tetrahydrododecyltrichlorosilane (C12); heptadecafluoro-1,1,2, 2-tetrahydrodecyltrichlorosilane (C10); nonafluoro-1,1,2,2-tetrahydrohexyltris(dimethylamino)silane; 3,3,3,4,4,5,5,6,6-nonafluorohexyltrichlorosilane; tridecafluoro-1,1,2,2-tetrahydrooctyltrichlorosilane (C8); bis(tridecafluoro-1,1,2, 2-tetrahydrooctyl)dimethylsiloxymethylchlorosilane; nonafluorohexyltriethoxysilane (C6); dodecyltrichlorosilane (DTS); dimethyldichlorosilane (DDMS); or 10-undecenyltrichlorosilane (V11); pentafluorophenylpropyltrichlorosilane (C5). Hydrophilic coatings include polymers such as polysaccharides, polyethylene glycol, polyamines, and polycarboxylic acids. Hydrophilic surfaces may also be created by oxygen plasma treatment of certain materials.

A coated surface may be formed by depositing a metal oxide onto a surface of the device. Example metal oxides useful for coating surfaces include, but are not limited to, $Al_2O_3$, $TiO_2$, $SiO_2$, or a combination thereof. Other metal oxides useful for surface modifications are known in the art. The metal oxide can be deposited onto a surface by standard deposition techniques, including, but not limited to, atomic layer deposition (ALD), physical vapor deposition (PVD), e.g., sputtering, chemical vapor deposition (CVD), or laser deposition. Other deposition techniques for coating surfaces, e.g., liquid-based deposition, are known in the art. For example, an atomic layer of $Al_2O_3$ can be deposited on a surface by contacting it with trimethylaluminum (TMA) and water.

In another approach, the device surface properties may be attributable to surface texture. For example, a surface may have a nanotexture, e.g., have a surface with nanometer surface features, such as cones or columns, that alters the wettability of the surface. Nanotextured surface may be hydrophilic, hydrophobic, or superhydrophobic, e.g., have a water contact angle greater than 150°. Exemplary superhydrophobic materials include Manganese Oxide Polystyrene ($MnO_2$/PS) nano-composite, Zinc Oxide Polystyrene (ZnO/PS) nano-composite, Precipitated Calcium Carbonate, Carbon nano-tube structures, and a silica nano-coating. Superhydrophobic coatings may also include a low surface energy material (e.g., an inherently hydrophobic material) and a surface roughness (e.g., using laser ablation techniques, plasma etching techniques, or lithographic techniques in which a material is etched through apertures in a patterned mask). Examples of low surface energy materials include fluorocarbon materials, e.g., polytetrafluoroethylene (PTFE), fluorinated ethylene propylene (FEP), ethylene tetrafluoroethylene (ETFE), ethylene chloro-trifluoroethylene (ECTFE), perfluoro-alkoxyalkane (PFA), poly(chloro-trifluoro-ethylene) (CTFE), perfluoro-alkoxyalkane (PFA), and poly(vinylidene fluoride) (PVDF). Other superhydrophobic surfaces are known in the art.

In some cases, the water contact angle of a hydrophilic or more hydrophilic material or coating is less than or equal to about 90°, e.g., less than 80°, 70°, 60°, 50°, 40°, 30°, 20°, or 10°, e.g., 90°, 85°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, or 0°. In some cases, the water contact angle of a hydrophobic or more hydrophobic material or coating is at least 70°, e.g., at least 80°, at least 85°, at least 90°, at least 95°, or at least 100° (e.g., about 100°, 101°, 102°, 103°, 104°, 105°, 106°, 107°, 108°, 109°, 110°, 115°, 120°, 125°, 130°, 135°, 140°, 145°, or about) 150°.

The difference in water contact angles between that of a hydrophilic or more hydrophilic material or coating and a hydrophobic or more hydrophobic material or coating may be 5° to 100°, e.g., 5° to 80°, 5° to 60°, 5° to 50°, 5° to 40°, 5° to 30°, 5° to 20°, 10° to 75°, 15° to 70°, 20° to 65°, 25° to 60°, 30 to 50°, 35° to 45°, e.g., 5°, 6°,7°,8°,9°,10°,15°, 20°, 25°, 30°, 35°, 40°, 45°, 50°, 55°, 60, 65°, 70°, 75°, 80°, 85°, 90°, 95°, or 100°.

The above discussion centers on the water contact angle. It will be understood that liquids employed in the devices and methods of the invention may not be water, or even aqueous. Accordingly, the actual contact angle of a liquid on a surface of the device may differ from the water contact angle. Furthermore, the determination of a water contact angle of a material or coating can be made on that material or coating when not incorporated into a device of the invention.

Particles

The invention includes devices, systems, and kits having particles, e.g., for use in analysis. The devices and systems are used for magnetic separation of samples containing magnetic particles. The samples may further include non-magnetic particles, e.g., attached to the magnetic particles. For example, particles configured with analyte moieties (e.g., barcode oligonucleotides, or nucleic acid barcode molecules), and optionally combined with binding molecules (e.g., proteins, peptides, aptamers, antibodies, or antibody fragments) and/or enzymes, substrates, etc.) can be included in a droplet containing an analyte (e.g., a cellular analyte) to modify the analyte and/or detect the presence or concentration of the analyte. In some embodiments, particles are synthetic particles (e.g., beads, e.g., gel beads). In one embodiment, the particles (e.g., beads) include analyte moieties (e.g., nucleic acid barcode molecules or barcode oligonucleotides).

Magnetic particles include at least one component that is responsive to a magnetic force. A magnetic particle may be entirely magnetic or may contain components that are non-magnetic. A magnetic particle may be a magnetic bead, e.g., a substantially spherical magnetic bead. The magnetic particle may be entirely magnetic or may contain one or more magnetic cores surrounded by one or more additional materials, such as, for example, one or more functional groups and/or modifications for binding one or more target molecules.

In some examples, a magnetic particle may contain a magnetic component and a surface modified with one or more silanol groups. Magnetic particles of this type may be used for binding target nucleic acid molecules. Silanol-modified magnetic beads are commercially available (Accu Bead silica-coated magnetic beads available from Bioneer, silane-modified Dynabeads available from Life Technologies, MagSi beads available from AMSBIO, among others). A magnetic particle may be a magnetic bead or particle and the surface may be functionalized with a plurality of carboxyl groups. Such magnetic particles can make use of solid phase reverse immobilization (SPRI) technology. Carboxylated magnetic beads are available from commercial sources, for example, Agencourt AMPure XP SPRI beads available from Beckman-Coulter.

Magnetic materials may be classified according to their magnetic properties. Without wishing to be bound by theory, materials can generally be classified as diamagnetic, paramagnetic, or ferromagnetic. Diamagnetism is a property of all materials and can be a weak magnetic force. Diamagnetic materials can create an induced magnetic field in a direction opposite to an externally applied magnetic field.

Paramagnetic materials can be attracted by an externally applied magnetic field and form induced magnetic fields in the direction of the applied magnetic field. Ferromagnetic materials are those that can be become permanently magnetized in the presence of a magnetic field. Examples of magnetic materials that may be included in a magnetic particle include iron, nickel, cobalt, composites thereof and alloys thereof. In some instances, a magnetic material may include one or more iron-oxides, such as magnetite or maghemite.

A particle, e.g., a magnetic particle or a bead, may be porous, non-porous, hollow (e.g., a microcapsule), solid, semi-solid, semi-fluidic, fluidic, and/or a combination thereof. In some instances, a particle, e.g., a bead, may be dissolvable, disruptable, and/or degradable. In some cases, a particle, e.g., a bead, may not be degradable. In some cases, the particle, e.g., a bead, may be a gel bead. A gel bead may be a hydrogel bead. A gel bead may be formed from molecular precursors, such as a polymeric or monomeric species. A semi-solid particle, e.g., a bead, may be a liposomal bead. Solid particles, e.g., beads, may comprise metals including iron oxide, gold, and silver. In some cases, the particle, e.g., the bead, may be a silica bead. In some cases, the particle, e.g., a bead, can be rigid. In other cases, the particle, e.g., a bead, may be flexible and/or compressible.

A particle, e.g., a magnetic particle or a bead, may comprise natural and/or synthetic materials. For example, a particle, e.g., a bead, can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the particle, e.g., the magnetic particle or bead, may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the particle, e.g., the bead, may comprise prepolymers, which are oligomers capable of further polymerization. For example, polyurethane beads may be prepared using prepolymers. In some cases, the particle, e.g., the bead, may contain individual polymers that may be further polymerized together. In some cases, particles, e.g., beads, may be generated via polymerization of different precursors, such that they comprise mixed polymers, co-polymers, and/or block co-polymers. In some cases, the particle, e.g., the bead, may comprise covalent or ionic bonds between polymeric precursors (e.g., monomers, oligomers, linear polymers), oligonucleotides, primers, and other entities. In some cases, the covalent bonds can be carbon-carbon bonds or thioether bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

Particles, e.g., magnetic particles or beads, may be of uniform size or heterogeneous size. In some cases, the diameter of a particle, e.g., a bead, may be at least about 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a particle, e.g., a bead, may have a diameter of less than about 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a particle, e.g., a bead, may have a diameter in the range of about 40-75 µm, 30-75 µm, 20-75 µm, 40-85 µm, 40-95 µm, 20-100 µm, 10-100 µm, 1-100 µm, 20-250 µm, or 20-500 µm. The size of a particle, e.g., a bead, e.g., a gel bead, used to produce droplets is typically on the order of a cross section of the first channel (width or depth). In some cases, the gel beads are larger than the width and/or depth of the first channel and/or shelf, e.g., at least 1.5x, 2x, 3x, or 4x larger than the width and/or depth of the first channel and/or shelf.

In certain embodiments, particles, e.g., magnetic particles or beads, can be provided as a population or plurality of particles, e.g., beads, having a relatively monodisperse size distribution. Where it may be desirable to provide relatively consistent amounts of reagents within droplets, maintaining relatively consistent particle, e.g., bead, characteristics, such as size, can contribute to the overall consistency. In particular, the particles, e.g., beads, described herein may have size distributions that have a coefficient of variation in their cross-sectional dimensions of less than 50%, less than 40%, less than 30%, less than 20%, and in some cases less than 15%, less than 10%, less than 5%, or less.

Particles may be of any suitable shape. Examples of particles, e.g., magnetic particles or beads, shapes include, but are not limited to, spherical, non-spherical, oval, oblong, amorphous, circular, cylindrical, and variations thereof.

A particle, e.g., magnetic particle or bead, may comprise releasably, cleavably, or reversibly attached analyte moieties (e.g., barcode oligonucleotides). A particle, e.g., bead, may comprise activatable analyte moieties (e.g., barcode oligonucleotides). A particle, e.g., bead may be a degradable, disruptable, or dissolvable particle, e.g., dissolvable bead.

As discussed above, analyte moieties (e.g., barcode oligonucleotide s) can be releasably, cleavably or reversibly attached to the particles, e.g., beads, such that analyte moieties (e.g., barcode oligonucleotides) can be released or be releasable through cleavage of a linkage between the barcode molecule and the particle, e.g., bead, or released through degradation of the particle (e.g., bead) itself, allowing the barcodes to be accessed or be accessible by other reagents, or both. Releasable analyte moieties (e.g., barcode oligonucleotides) may sometimes be referred to as activatable analyte moieties (e.g., activatable barcodes), in that they are available for reaction once released. Thus, for example, an activatable analyte moiety (e.g., activatable barcode) may be activated by releasing the analyte moiety (e.g., barcode) from a particle, e.g., bead (or other suitable type of droplet described herein). Other activatable configurations are also envisioned in the context of the described methods and systems.

In addition to, or as an alternative to the cleavable linkages between the particles, e.g., magnetic particles or beads, and the associated moieties, such as barcode containing nucleic acids (e.g., oligonucleotides), the particles, e.g., beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a particle, e.g., bead, may be dissolvable, such that material components of the particle, e.g., bead, are degraded or solubilized when exposed to a particular chemical species or an environmental change, such as a change temperature or a change in pH. In some cases, a gel bead can be degraded or dissolved at elevated temperature and/or in basic conditions. In some cases, a particle, e.g., bead, may be thermally degradable such that when the particle, e.g., bead, is exposed to an appropriate change in temperature (e.g., heat), the particle, e.g., bead, degrades.

Degradation or dissolution of a particle (e.g., bead) bound to a species (e.g., a nucleic acid, e.g., an oligonucleotide, e.g., barcoded oligonucleotide) may result in release of the species from the particle, e.g., bead. As will be appreciated from the above disclosure, the degradation of a particle, e.g., bead, may refer to the disassociation of a bound or entrained species from a particle, e.g., bead, both with and without structurally degrading the physical particle, e.g., bead, itself. For example, entrained species may be released from particles, e.g., beads, through osmotic pressure differences due to, for example, changing chemical environments. By way of example, alteration of particle, e.g., bead, pore sizes due to osmotic pressure differences can generally occur without structural degradation of the particle, e.g., bead, itself. In some cases, an increase in pore size due to osmotic swelling of a particle (e.g., bead or a liposome), can permit the release of entrained species within the particle. In other cases, osmotic shrinking of a particle may cause the particle, e.g., bead, to better retain an entrained species due to pore size contraction.

Any suitable number of analyte moieties (e.g., molecular tag molecules (e.g., primer, barcoded oligonucleotide, etc.)) can be associated with a particle, e.g., bead, such that, upon release from the particle, the analyte moieties (e.g., molecular tag molecules (e.g., primer, e.g., barcoded oligonucleotide, etc.)) are present in the droplet at a pre-defined concentration. Such pre-defined concentration may be selected to facilitate certain reactions for generating a sequencing library, e.g., amplification, within the droplet. In some cases, the pre-defined concentration of a primer can be limited by the process of producing oligonucleotide-bearing particles, e.g., beads.

Additional reagents may be included as part of the particles (e.g., analyte moieties), for example, to activate, mediate, or otherwise participate in a reaction, e.g., between the analyte and analyte moiety.

Biological Samples

Samples may include biological particles (e.g., cells or particulate components thereof, e.g., organelles, such as a nucleus or a mitochondrion) and/or macromolecular constituents thereof (e.g., components of cells (e.g., intracellular or extracellular proteins, nucleic acids, glycans, or lipids) or products of cells (e.g., secretion products)). An analyte from a biological particle, e.g., component or product thereof, may be considered to be a bioanalyte. In some embodiments, a biological particle, e.g., cell, or product thereof is included in a droplet, e.g., with one or more particles (e.g., beads) having an analyte moiety. A biological particle, e.g., cell, a nucleus, and/or components or products thereof can, in some embodiments, be encased inside a gel, such as via polymerization of a droplet containing the biological particle and precursors capable of being polymerized or gelled.

Cellular analytes, or analytes originating from biological particles (e.g., cells or nuclei), may be used and may include, without limitation, any or all molecules or substances from or produced by a cell. Chemically, cellular analytes may include proteins, polypeptides, peptides, saccharides, polysaccharides, lipids, nucleic acids, combinations thereof and other biomolecules. A cellular analyte may include a protein, a metabolite, a metabolic byproduct, an antibody or antibody fragment, an enzyme, an antigen, a carbohydrate, a lipid, a macromolecule, or a combination thereof (e.g., proteoglycan) or other biomolecule. The cellular analyte may be a nucleic acid molecule. The cellular analyte may be a deoxyribonucleic acid (DNA) molecule or a ribonucleic acid (RNA) molecule. The DNA molecule may be a genomic DNA molecule. The cellular analyte may include coding or non-coding RNA. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA.

In some instances, the analytes may be contained in a sample. A sample may contain only analytes or may contain analytes in addition to one or more additional components. In some examples, the sample may contain biological particles. In some examples, biological particles may be cells, parts of cells or cell organelles, like a cell nucleus. A biological particle may include a cell, without any limitation on the kind or type of cell. Cells may be eukaryotic, prokaryotic or archaea. Cells may be eukaryotic cells from a cell line or cell culture sample. A cell may be a mammalian cell. A cell may be an animal cell. A cell may be a human cell. A cell may be from a cell culture. A cell may be from an immortalized cell line. A cell may be from a primary sample, such as a patient sample. A cell may be from a frozen stock of cells (e.g., cryopreserved cells). The cells may be adherent cells or suspension cells. The cells may be from a tissue sample, such as a biopsy, core biopsy, needle aspirate, or fine needle aspirate. The sample containing cells may come from bodily fluids, such as blood, urine or saliva. The sample may be a skin sample. The sample may be a cheek swab. The sample may contain peripheral blood mononuclear cells (PBMCs). Samples that include parts of or organelles from cells are also encompassed by this disclosure. In some examples, a sample may contain a cell nucleus from a eukaryotic cell.

Cells include, for example, a plant cell, animal cell, human cell, insect-derived cells, bacteria, algae, cardiomyocytes, stem cells, neurons, primary neurons, embryonic stem cells (ESCs), induced pluripotent stem cells (iPSCs), hepatocytes, primary heart valve cells, primary hematopoietic cells, gastrointestinal cells, lymphocytes, T-cells, B-cells, natural killer cells, dendritic cells, hematopoietic cells, beta cells, somatic cells, germ cells, embryos (human and animal), zygotes, gametes, and other types of cells.

In the case of encapsulated biological particles (e.g., cells, nuclei, or particulate components thereof), a biological particle may be included in a droplet that contains lysis reagents in order to release the contents (e.g., contents containing one or more analytes (e.g., bioanalytes)) of the biological particles within the droplet. In such cases, the lysis agents can be contacted with the biological particle suspension concurrently with, or immediately prior to the introduction of the biological particles a droplet or particle. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be contained in a droplet with the biological particles (e.g., cells, nuclei, or particulate components thereof) to cause the release of the biological particles' contents into the droplets or particles. For example, in some cases, surfactant based lysis solutions may be used to lyse cells, although these may be less desirable for emulsion based systems where the surfactants can interfere with stable emulsions. In some cases, lysis solutions may include non-ionic surfactants such as, for example, TRITON X-100 and TWEEN 20. In some cases, lysis solutions may include ionic surfactants such as, for example, sarcosyl and sodium dodecyl sulfate (SDS). In some embodiments, lysis solutions are hypotonic, thereby lysing cells by osmotic shock.

Electroporation, thermal, acoustic or mechanical cellular disruption may also be used in certain cases, e.g., non-emulsion-based droplet formation such as encapsulation of biological particles that may be in addition to or in place of droplet formation, where any pore size of the encapsulate is sufficiently small to retain nucleic acid fragments of a desired size, following cellular disruption.

In addition to the lysis agents, other reagents can also be included in droplets with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles (e.g., cells, nuclei, or particulate components thereof), the biological particles may be exposed to an appropriate stimulus to release the biological particles or their contents from a particle (e.g., a bead or a microcapsule) within a droplet. For example, in some cases, a chemical stimulus may be included in a droplet along with an encapsulated biological particle to allow for degradation of the encapsulating matrix and release of the cell or its contents into the larger droplet. In some cases, this stimulus may be the same as the stimulus described elsewhere herein for release of analyte moieties (e.g., oligonucleotides) from their respective particle (e.g., bead). In alternative aspects, this may be a different and non-overlapping stimulus, in order to allow an encapsulated biological particle to be released into a droplet at a different time from the release of analyte moieties (e.g., oligonucleotides) into the same droplet.

Additional reagents may also be included in droplets with the biological particles, such as endonucleases to fragment a biological particle's DNA, DNA polymerase enzymes and dNTPs used to amplify the biological particle's nucleic acid fragments and to attach the barcode molecular tags to the amplified fragments. Other reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyinosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 , 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 nucleotides or longer.

In some cases, the length of a switch oligo may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 , 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 , 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells or nuclei are released into their respective droplets, the macromolecular components (e.g., macromolecular constituents of biological particles, such as RNA, DNA, or proteins) contained therein may be further processed.

As described above, the macromolecular components (e.g., bioanalytes) of individual biological particles (e.g., cells, nuclei, or particulate components thereof) can be provided with unique identifiers (e.g., barcode oligonucleotides) such that upon characterization of those macromolecular components, at which point components from a heterogeneous population of cells or nuclei may have been mixed and are interspersed or solubilized in a common liquid, any given component (e.g., bioanalyte) may be traced to the biological particle (e.g., cell) or nucleus from which it was obtained. The ability to attribute characteristics to individual biological particles or groups of biological particles is provided by the assignment of unique identifiers specifically to an individual biological particle or groups of biological particles. Unique identifiers, for example, in the form of nucleic acid barcodes, can be assigned or associated with individual biological particles (e.g., cells, nuclei, or particulate components thereof) or populations of biological particles (e.g., cells or nuclei), in order to tag or label the biological particle's macromolecular components (and as a result, its characteristics) with the unique identifiers. These unique identifiers can then be used to attribute the biological particle's components and characteristics to an individual biological particle or group of biological particles. This can be performed by forming droplets including the individual biological particle or groups of biological particles with the unique identifiers (via particles, e.g., beads), as described in the systems and methods herein.

In some aspects, the unique identifiers are provided in the form of oligonucleotides that comprise nucleic acid barcode sequences that may be attached to or otherwise associated with the nucleic acid contents of individual biological particle, or to other components of the biological particle, and particularly to fragments of those nucleic acids. The oligonucleotides are partitioned such that as between oligonucleotides in a given droplet, the nucleic acid barcode sequences contained therein are the same, but as between different droplets, the oligonucleotides can, and do have differing barcode sequences, or at least represent a large number of different barcode sequences across all of the droplets in a given analysis. In some aspects, only one nucleic acid barcode sequence can be associated with a given droplet, although in some cases, two or more different barcode sequences may be present.

The nucleic acid barcode sequences can include from 6 to about 20 or more nucleotides within the sequence of the oligonucleotides. In some cases, the length of a barcode sequence may be 6, 7, 8, 9, 10, 11, 12, 13, 14, 15, 16, 17, 18, 19, 20 nucleotides or longer. In some cases, the length of a barcode sequence may be at least 6, 7, 8, 9, 10, 11, 12, 13, 14, 15, 16, 17, 18, 19, 20 nucleotides or longer. In some cases, the length of a barcode sequence may be at most 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be 4, 5, 6, 7, 8, 9, 10, 11, 12, 13, 14, 15, 16 nucleotides or longer. In some cases, the barcode subsequence may be at least 4, 5, 6, 7, 8, 9, 10, 11, 12, 13, 14, 15, 16 nucleotides or longer. In some cases, the barcode subsequence may be at most 4, 5, 6, 7, 8, 9, 10, 11, 12, 13, 14, 15, 16 nucleotides or shorter.

Analyte moieties (e.g., oligonucleotides) in droplets can also include other functional sequences useful in processing of nucleic acids from biological particles contained in the droplet. These sequences include, for example, targeted or random/universal amplification primer sequences for amplifying the genomic DNA from the individual biological particles within the droplets while attaching the associated barcode sequences, sequencing primers or primer recognition sites, hybridization or probing sequences, e.g., for identification of presence of the sequences or for pulling down barcoded nucleic acids, or any of a number of other potential functional sequences.

Other mechanisms of forming droplets containing oligonucleotides may also be employed, including, e.g., coalescence of two or more droplets, where one droplet contains oligonucleotides, or microdispensing of oligonucleotides into droplets, e.g., droplets within microfluidic systems.

In an example, particles (e.g., magnetic particles or beads) are provided that each include large numbers of the above described barcoded oligonucleotides releasably attached to the beads, where all of the oligonucleotides attached to a particular bead will include the same nucleic acid barcode sequence, but where a large number of diverse barcode sequences are represented across the population of beads used. In some embodiments, hydrogel beads, e.g., beads having polyacrylamide polymer matrices, are used as a solid support and delivery vehicle for the oligonucleotides into the droplets, as they are capable of carrying large numbers of oligonucleotide molecules and may be configured to release those oligonucleotides upon exposure to a particular stimulus, as described elsewhere herein. In some cases, the population of beads will provide a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of oligonucleotide molecules attached. In particular, the number of molecules of oligonucleotides including the barcode sequence on an individual bead can be at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules, or more.

Moreover, when the population of magnetic particles or beads are included in droplets, the resulting population of droplets can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each droplet of the population can include at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules.

In some cases, it may be desirable to incorporate multiple different barcodes within a given droplet, either attached to a single particle or multiple particles, e.g., beads, within the droplet. For example, in some cases, mixed, but known barcode sequences set may provide greater assurance of identification in the subsequent processing, for example, by providing a stronger address or attribution of the barcodes to a given droplet, as a duplicate or independent confirmation of the output from a given droplet.

Oligonucleotides may be releasable from the particles (e.g., beads) upon the application of a particular stimulus. In some cases, the stimulus may be a photo-stimulus, e.g., through cleavage of a photo-labile linkage that releases the oligonucleotides. In other cases, a thermal stimulus may be used, where increase in temperature of the particle, e.g., bead, environment will result in cleavage of a linkage or other release of the oligonucleotides form the particles, e.g., beads. In still other cases, a chemical stimulus is used that cleaves a linkage of the oligonucleotides to the beads, or otherwise results in release of the oligonucleotides from the particles, e.g., magnetic particles or beads. In one case, such compositions include the polyacrylamide matrices described above for encapsulation of biological particles and may be degraded for release of the attached oligonucleotides through exposure to a reducing agent, such as dithiothreitol (DTT).

Kits and Systems

Devices of the invention may be combined with various external components in the form of kits and systems. For example, a system or kit may include a device of the invention and, e.g., one or more sample holders, magnetic sources, e.g., magnets, samples, magnetic particles, and the like. The system or kit may include a plurality of sample holders, vessels, outer vessels, filters, walls, and/or magnetic sources. The kits and systems may further include, e.g., electrodes, pumps, reservoirs, controllers, reagents, e.g., analyte moieties, liquids, and/or particles (e.g., beads).

Methods

The methods of magnetic separation described herein are used for separating or sorting particles in a liquid by providing a device or system that includes magnetic source having at least one sharp feature, e.g., with a corner radius of less than about 10 mm, e.g., less than about 1 mm, or producing a magnetic gradient of at least 10 T/m, e.g., at least 100 T/m, 1,000 T/m, 10,000 T/m, 100,000 T/m, e.g., at least 10,000,000 T/m, that is operably coupled to a housing that contains a receptacle for a sample holder. The method may include providing a sample holder that contains a liquid with suspended magnetic particles. The sample holder is then placed in the receptacle of the device, and the magnetic particles within the sample are immobilized at a location or plurality of locations in the sample holder, e.g., adjacent to the magnetic source(s).

The method may further include removing the liquid from the sample holder, e.g., to remove non-magnetic particles or debris. Removing the liquid may include decanting, suctioning, or pipetting the liquid from the sample holder. The method may further include washing the magnetic particles or particles separated therefrom. The method may include resuspending the magnetic particles in a second liquid, e.g., to produce a sample that is enriched in the magnetic particles. Removing the liquid and resuspending the particles may be performed one or more times, e.g., to serially enrich or purify the magnetic particles. The sample containing purified magnetic particles may be subsequently used to produce droplets containing the particles.

In an embodiment with a device having a lumen, the method of magnetic separation includes providing a device and optionally an outer vessel. The vessel includes a liquid with suspended magnetic particles. Sample can be moved through the lumen by any suitable force, e.g., by centrifuging or applied pressure (e.g., pneumatic or hydrodynamic), and the magnetic particles are immobilized at a location adjacent the magnetic source. Non-magnetic particles and solutes, such as debris within a sample, may exit the lumen through the outlet. Non-magnetic particles may collect in an outer vessel or in a reservoir or on a filter in the vessel.

Figure 3:
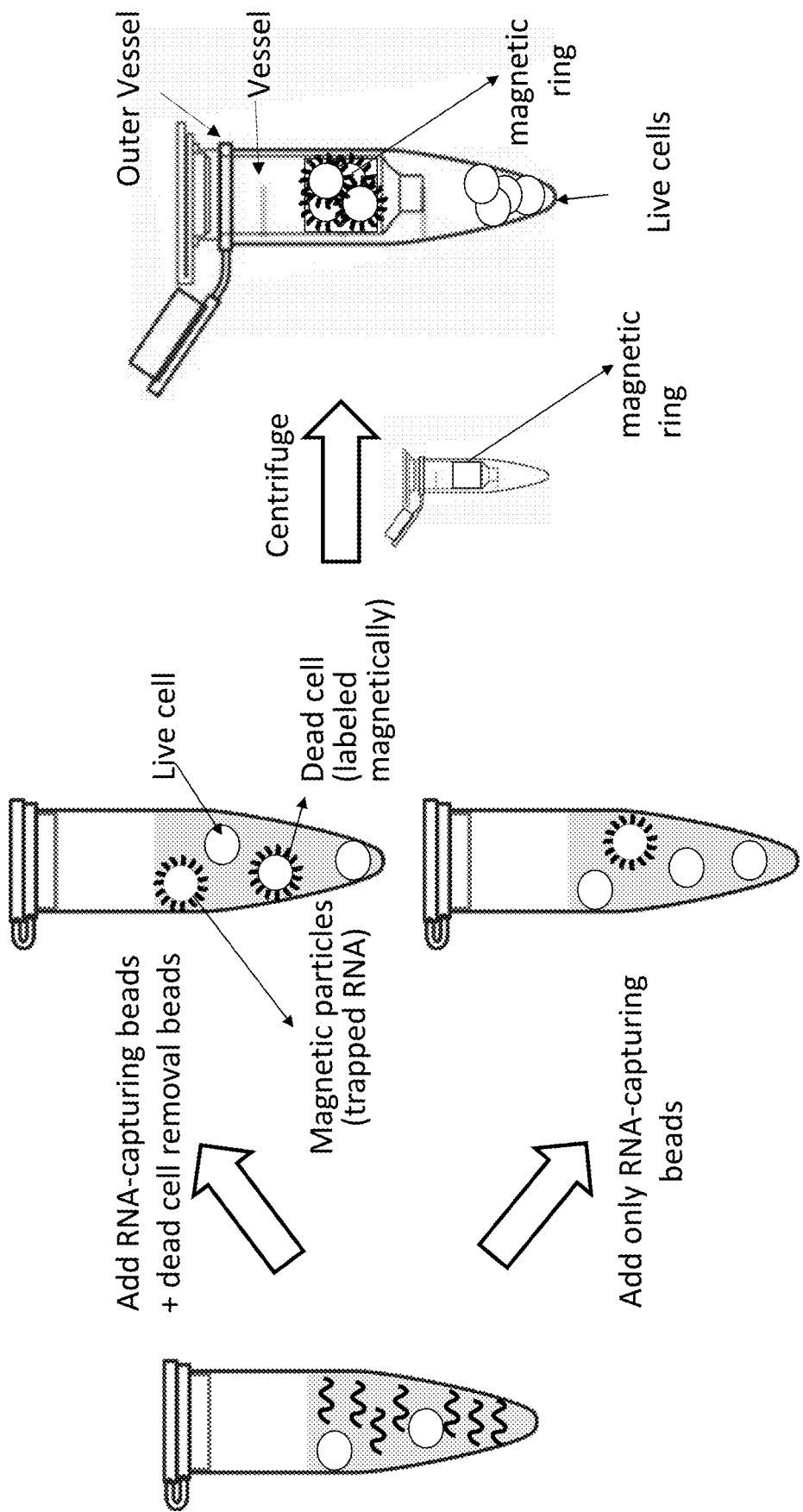
FIG. 3 is a schematic drawing of a workflow using a device of the invention that includes a vessel having a lumen with an inlet and an outlet and a magnetic ring. A user can add magnetic particles to a biological sample to trap extracellular molecules (e.g., RNA) and dead cells (top panel) or extracellular molecules (e.g., RNA) only (bottom panel). Once the magnetic beads trap their associated targets, the sample containing the magnetic particles can be centrifuged in the device. The magnetic particles are attracted to a magnetic ring within the device, while the nonmagnetic particles pass through the outlet of the lumen and are collected at the bottom of an outer vessel.

The method may initially include a step of providing magnetic beads to capture certain biological particles, such as cells (e.g., dead or live cells) or nuclei and/or macromolecular constituents of a cell (e.g., proteins or nucleic acids, e.g., RNA) depending on the desired type of separation (FIG. 3).

The method may further include removing the liquid from the vessel or outer vessel, e.g., to remove non-magnetic particles or debris. Removing the liquid may include decanting, suctioning, or pipetting the liquid from the outer vessel or vessel. The method may further include washing the magnetic particles or particles separated therefrom. The method may include resuspending the magnetic particles or particles separated therefrom in a second liquid, e.g., to produce a sample that is enriched in the magnetic particles or particles separated therefrom. Removing the liquid and resuspending the particles may be performed one or more times, e.g., to serially enrich or purify desired particles.

In some embodiments, the non-magnetic particles are desired, e.g., for subsequent use. In such an embodiment, the non-magnetic particles are collected from the outer vessel or vessel.

In an embodiment in which the device contains a baffle disposed in the lumen, the particles may be directed in the lumen, e.g., towards the side of the vessel.

Figure 4:
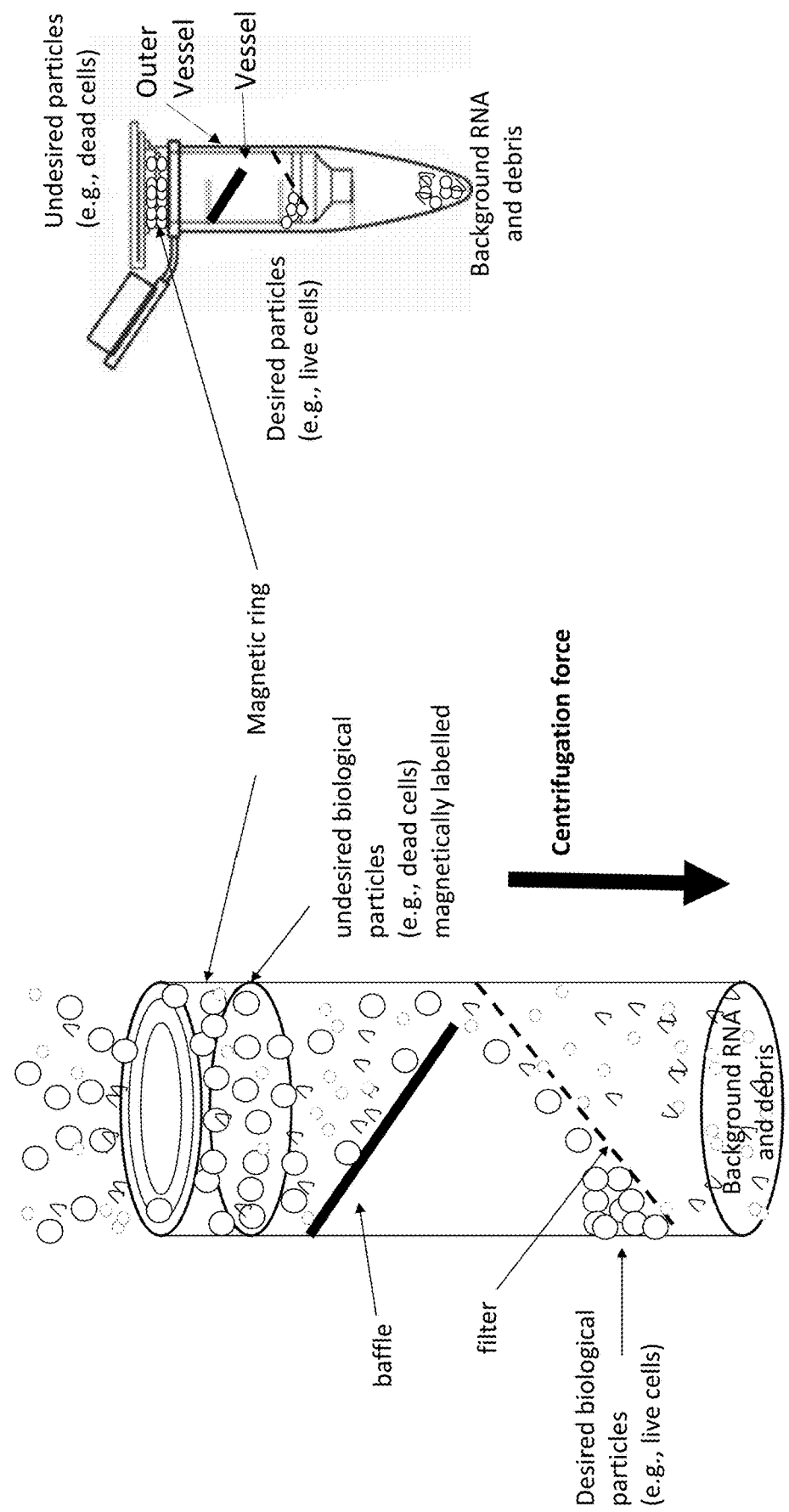
FIG. 4 is a schematic drawing of a device as that includes a vessel having a lumen with an inlet and an outlet and a magnetic ring. The device also includes a baffle (or wall) and a filter in the lumen of the vessel. During centrifugation, magnetic particles are attracted to a magnetic ring within the vessel, while the nonmagnetic particles pass through the outlet of the lumen are collected in the outer vessel. The baffle (or wall) disposed in the lumen deflects the particles and the filter has openings configured to allow extracellular molecules (e.g., background RNA) and debris to pass through while trapping desired biological particles (e.g., live cells) on the filter.

In an embodiment in which the device contains a filter, upon centrifugation or applied pressure, the filter traps particles of a predetermined size. For example, the filter may be sized to trap desired cells or nuclei (e.g., for subsequent use), while smaller particles and solutes, such as background RNA and cellular debris can pass through the filter (FIG. 4).

The centrifugation angle may be tuned, e.g., to suit a particular mode of separation. Furthermore, the angle of the baffle and/or filter can be set to suit a particular mode of separation, e.g., depending on the size of particles and/or the openings within the filter.

The methods described herein may be used to move magnetic particles (e.g., cause spatial separation), separate different species of magnetic particles, or to produce a population enriched in particular magnetic particles from a mixture. For example, the population may be enriched by 10%. The mixture may be enriched (e.g., by 10%, 20%, 30%, 40%, 50%, 60%, 70%, 80%, 100%, 200%, 300%, 400%, 500%, 600%, 700%, 800%, 900%, 1000%, or more) for a subset of the particles. The enrichment of the mixture may be used to remove contaminants or undesired particles in the solution (e.g., solute molecules, insoluble contaminants, debris, soluble components, etc.). Accordingly, the enrichment may be relative to the original mixture.

One or more magnetic particles can be isolated and/or immobilized at a location in the sample holder or vessel by applying a magnetic force to the one or more magnetic particles (e.g., magnetic separation). A magnetic force can be applied to one or more magnetic particles by exposing the one or more magnetic particles to an external magnetic field produced by the magnetic source, e.g., with a sharp feature. The magnetic source may be, for example, a permanent magnetic, electromagnet, or the like. The magnetic responsiveness of a magnetic particle to a magnetic force can be useful in isolating a magnetic particle having bound target from a mixture. Application of a magnetic force to the magnetic particle can result in separation of the magnetic particle from other components in a mixture. Accordingly, any target (e.g., one or more target cells or molecules) that is also bound to the magnetic particle, covalently or non-covalently, can also be separated from non-bound components in a mixture. When an external magnetic field is applied to a magnetic particle, the magnetic particle can be attracted via magnetic force in the direction of the external magnetic field. The magnetic source can be positioned such that a magnetic particle or a plurality of magnetic particles is attracted to one or more specific locations, e.g., in the sample holder or vessel. For example, when one or more magnetic particles are provided to a mixture in a sample holder or vessel, the one or more magnetic particles may be positioned at one or more locations (e.g., surfaces) of the sample holder vessel. For example, a magnetic source can immobilize a magnetic particle at the bottom of a sample holder or vessel. In some cases, a magnetic source can immobilize a magnetic particle on a side wall of a sample holder or vessel. In some instances, a plurality of magnetic sources can immobilize a magnetic particle at a plurality of locations within the sample holder or vessel.

Magnetic immobilization/separation of one or more magnetic particles at multiple positions within a sample holder may be used in purification. Magnetic separation at multiple positions within a sample holder may occur simultaneously (e.g., one or more magnetic particles simultaneously positioned at a plurality of locations within a sample holder) or sequentially (e.g., a first round of magnetic separation at a first location, a second round or magnetic separation at a second location, etc.). For example, one or more magnetic particles may be provided to a sample holder comprising a liquid mixture comprising contents that contain one or more targets, e.g., following breaking of droplets or for subsequent incorporation into droplets. The one or more magnetic particles can bind the target to provide one or more bound targets. Following binding of targets to the one or more magnetic particles, the one or more magnetic particles can be immobilized at a first location of the sample holder via the magnetic source, thereby separating or isolating the one or more magnetic particles (and associated targets) from the mixture. For example, an external magnetic field may be applied to the sample holder such that a magnetic particle with a bound target within the sample holder is attracted or pulled towards the magnetic source. Immobilized magnetic particles may be in the form of a pellet or plurality of pellets at the bottom or on the wall of the sample holder. Generally, an immobilized magnetic particle can be segregated in a sample holder and the movement of the immobilized magnetic particle can be restricted (e.g., to the bottom of or the wall of a sample holder).

The sorting of particles may be used to enrich a mixture of particles for a desired species before formation of droplets. For example, the sorting may be used to enrich a mixture of cells, nuclei, or particulate components thereof for a desired species of cell (e.g., type of cell) or particulate component thereof (e.g., organelles, such as nuclei or mitochondria). The methods described herein may further include producing droplets containing the particles. By sorting the particles before producing the droplets, a larger fraction of the droplets will contain the desired species and/or number of particles within the droplet, and a reduced fraction of droplets will contain undesired species and/or number of droplets.

In some embodiments, the methods of separation allow a user to produce a population of particles having desired characteristics. For example, in some embodiments, following magnetic separation and incorporation into droplets, the method generates populations of droplets or particles that include a suitable fraction of desired droplets or particles (e.g., from 50% to 100%, from 60% to 100%, from 70% to 100%, from 80% to 100%, from 90% to 100%, or from 95% to 100% of droplets). In some embodiments, at least 10% e.g., at least 20%, 30%, 40%, 50%, 60%, 70%, 80%, 85%, 90%, 95%, 97%, 99%, or 100%, of the droplets or particles are usable for a desired purpose.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Devices, systems, compositions, and methods of the present disclosure may be used for various applications, such as, for example, processing a single analyte (e.g., bioanalytes, e.g., RNA, DNA, or protein) or multiple analytes (e.g., bioanalytes, e.g., DNA and RNA, DNA and protein, RNA and protein, or RNA, DNA and protein) from a single cell or nucleus. For example, a biological particle (e.g., a cell, a nucleus, or virus) can be formed in a droplet, and one or more analytes (e.g., bioanalytes) from the biological particle (e.g., cell or nucleus) can be modified or detected (e.g., bound, labeled, or otherwise modified by an analyte moiety) for subsequent processing. The multiple analytes may be from the single cell or nucleus. This process may enable, for example, proteomic, transcriptomic, and/or genomic analysis of the cell/nucleus or population thereof (e.g., simultaneous proteomic, transcriptomic, and/or genomic analysis of the cell/nucleus or population thereof).

Methods of modifying analytes include providing a plurality of particles (e.g., beads) in a liquid carrier (e.g., an aqueous carrier); providing a sample containing an analyte (e.g., as part of a cell, a nucleus or component or product thereof) in a sample liquid; and using the device to combine the liquids and form an analyte droplet containing one or more particles and one or more analytes (e.g., as part of one or more cells, nuclei, or components or products thereof). Such sequestration of one or more particles with analyte (e.g., bioanalyte associated with a cell or a nucleus) in a droplet enables labeling of discrete portions of large, heterologous samples (e.g., single cells or nuclei within a heterologous population). Once labeled or otherwise modified, droplets or particles can be subsequently sorted or combined (e.g., by breaking an emulsion), and the resulting liquid can be analyzed to determine a variety of properties associated with each of numerous single cells or nuclei.

The invention also provides methods of single-cell (or single-nucleus) nucleic acid sequencing, in which a heterologous population of cells/nuclei can be characterized by their individual gene expression, e.g., relative to other cells/nuclei of the population. Methods of barcoding cells/nuclei discussed above and known in the art can be part of the methods of single-cell (or single nucleus) nucleic acid sequencing provided herein. After barcoding, nucleic acid transcripts that have been barcoded are sequenced, and sequences can be processed, analyzed, and stored according to known methods. In some embodiments, these methods enable the generation of a genome library containing gene expression data for any single cell or nucleus within a heterologous population.

In one aspect, the present disclosure provides methods for removing or depleting unwanted components (e.g., dead cells or extracellular molecules) from a sample with biological particles. In one embodiment, the method includes providing a sample with biological particles and unwanted components originating from biological particles (e.g., live or dead cells). In an additional embodiment, the biological particles are live (or intact) cells or intact nuclei. In another embodiment, the unwanted components include one or more of dead or dying cells, non-intact nuclei, extracellular analytes or molecules, and other debris. In one embodiment, the method further includes magnetically labelling the biological particles to provide a suspension (e.g., an aqueous suspension or liquid) with magnetically labelled biological particles and unwanted components that are un-labelled, i.e., not magnetically labelled. In one other embodiment, the method includes providing a device for magnetic separation that includes a housing with a receptacle for a sample holder (e.g., a tube) and a magnetic source operably connected to the receptacle as further described herein. In one embodiment, the magnetic source includes at least one feature with a corner radius of less than about 1 mm or producing a magnetic gradient of at least about 100,000 T/m. The method further includes dispensing the suspension into a sample holder, which can then be inserted into the receptacle. In one further embodiment, the device is subjected to conditions to allow the magnetically labelled biological particles to be immobilized at a location in the sample. In one embodiment, the location is a location that is adjacent to the magnetic source, e.g., at an inner wall of the sample holder where the sample holder is a tube. In one other embodiment, the method further includes recovering the immobilized magnetically labelled biological particles such that the unwanted components are absent from or depleted from the recovered biological particles. Other features of the device, including the housing, receptacle, sample holder, and magnetic source are further described herein.

In one other aspect, the present disclosure provides an alternative method for removing or depleting unwanted components (e.g., dead cells or extracellular molecules) from a sample with biological particles. In one embodiment, the method includes providing a sample with biological particles and unwanted components originating from biological particles (e.g., live or dead cells). In an additional embodiment, the biological particles are live (or intact) cells or intact nuclei. In an additional embodiment, the biological particles are live (or intact) cells or intact nuclei. In another embodiment, the unwanted components include one or more of dead or dying cells, non-intact nuclei, extracellular analytes or molecules, and other debris. In one embodiment, the method includes magnetically labelling unwanted components (e.g., dead cells) and/or magnetically capturing or trapping unwanted components (e.g., extracellular molecules, such as background RNA) in the sample to provide a suspension (e.g., an aqueous suspension or liquid) with unwanted components that are magnetically labelled and biological particles (e.g., live cells) that are un-labelled, i.e., not magnetically labelled. In the case of unwanted extracellular molecules, a magnetic particle configured to bind or trap such molecules may be used. In one other embodiment, the method includes providing a device for magnetic separation that includes a vessel having a lumen with an inlet and an outlet (e.g., a spin column) and a magnetic source disposed to exert a magnetic field in the lumen, wherein the device optionally further includes an outer vessel (e.g., a tube) in which the vessel is disposed, as further described herein. In one embodiment, the method further includes dispensing the suspension into the lumen, e.g., via the inlet. In a further embodiment, the device is subjected to conditions that allow the unwanted components that are magnetically labelled to be immobilized at a location in the sample. In one embodiment, the location is a location that is adjacent to the magnetic source, e.g., at an inner wall of the lumen. In another embodiment, the device is subjected to conditions that allow the un-labelled biological particles to migrate away from the magnetic source and/or out of the vessel. In one embodiment, the un-labelled biological particles to migrate out of the vessel via the outlet. In another embodiment, a fluid (or suspension or liquid) including the un-labelled biological particles passing through or migrating out of the vessel is captured or collected in the outer vessel. Other features of the device, including the vessel, lumen, baffle, filter, and magnetic source are further described herein.

In one other aspect, the present disclosure provides an additional alternative method for removing or depleting unwanted components (e.g., dead cells or extracellular molecules) from a sample with biological particles. In one embodiment, the method includes providing a sample with biological particles and unwanted components originating from biological particles (e.g., live or dead cells). In an additional embodiment, the biological particles are live (or intact) cells or intact nuclei. In an additional embodiment, the biological particles are live (or intact) cells or intact nuclei. In another embodiment, the unwanted components include one or more of dead or dying cells, non-intact nuclei, extracellular analytes or molecules, and other debris. In one embodiment, the method includes magnetically labelling unwanted components (e.g., dead cells) in the sample to provide a suspension (e.g., an aqueous suspension or liquid) with unwanted components that are magnetically labelled, unwanted components that are un-labelled, i.e., not magnetically labelled, and biological particles (e.g., live cells) that are un-labelled, i.e., not magnetically labelled. In one other embodiment, the method includes providing a device for magnetic separation that includes a vessel having a lumen with an inlet and an outlet (e.g., a spin column) and a magnetic source disposed to exert a magnetic field in the lumen. In another embodiment, the vessel further includes a baffle disposed at an angle relative to a horizontal cross-section of the lumen and/or a filter disposed at an angle relative to a horizontal cross-section of the lumen. The filter may be positioned in the lumen at or upstream of the outlet and/or configured to trap biological particles of a predetermined size, e.g., the un-labelled biological particles. In one additional embodiment, the device further includes an outer vessel (e.g., a tube) in which the vessel is disposed, as further described herein. In one embodiment, the method further includes dispensing the suspension into the lumen, e.g., via the inlet. In a further embodiment, the device is subjected to conditions that allow the unwanted components that are magnetically labelled to be immobilized at a location in the sample. In one embodiment, the location is a location that is adjacent to the magnetic source, e.g., at an inner wall of the lumen. In another embodiment, the device is subjected to conditions that allow the un-labelled unwanted components and biological particles to migrate away from the magnetic source and/or towards the baffle. In one other embodiment, the device is subjected to conditions that allow the un-labelled unwanted components and biological particles to migrate from the baffle towards the filter. In one embodiment, the un-labelled biological particles are trapped by the filter while the un-labelled unwanted components are not trapped by the filter and instead pass through the filter towards the outlet. In one embodiment, the un-labelled unwanted components migrate out of the vessel via the outlet. In another embodiment, a fluid (or suspension or liquid) with the un-labelled biological particles trapped by the filter is captured or collected from the vessel while the magnetically labelled unwanted components are retained in the lumen and the un-labelled unwanted components are retained in the outer vessel. Other features of the device, including the vessel, lumen, baffle, filter, and magnetic source are further described herein.

EXAMPLES

The following examples describe devices and methods for magnetic separation.

Example 1

FIG. 1 is a schematic drawing of a device that includes a permanent magnet that surrounds a sample holder. A liquid containing a mixture of magnetic and unlabeled particles is within the sample holder. As the sample holder is placed within a housing that includes a receptacle for the sample holder and the magnet, the magnetic particles are attracted by the magnet and become immobilized at the edge of the sample holder. The unlabeled particles are not attracted and do not move towards to the edge of the sample holder.

Figure 2A:
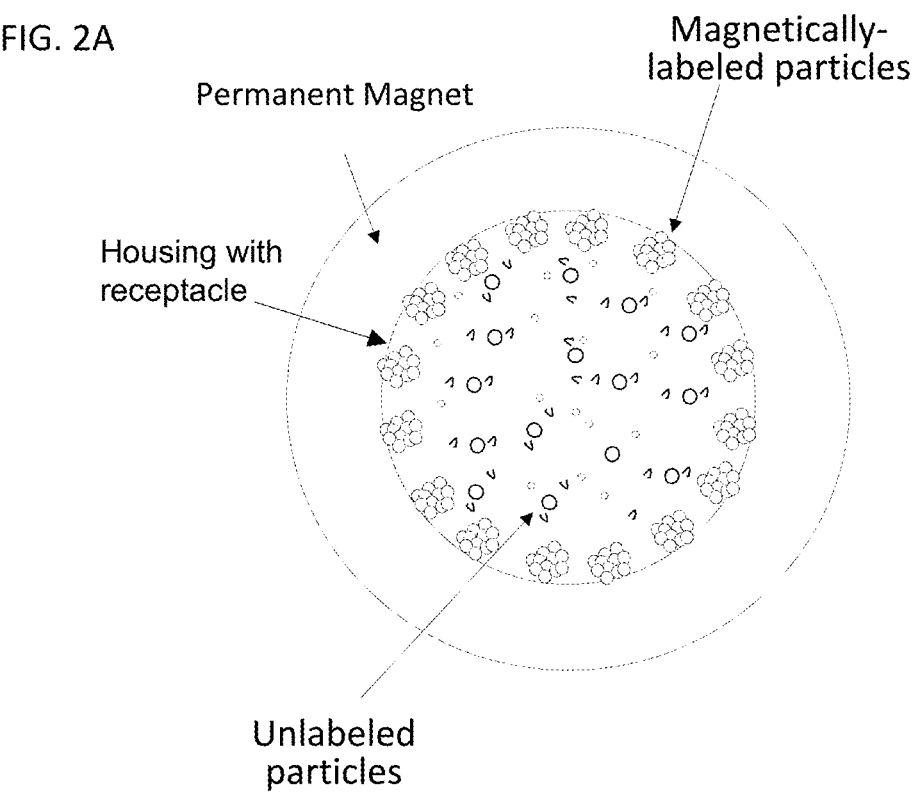
FIGS. 2A and 2B are schematic drawings of a device that includes a permanent magnet with sharp features that surrounds a sample holder containing a liquid with a mixture of magnetic and unlabeled particles.
Figure 2B:
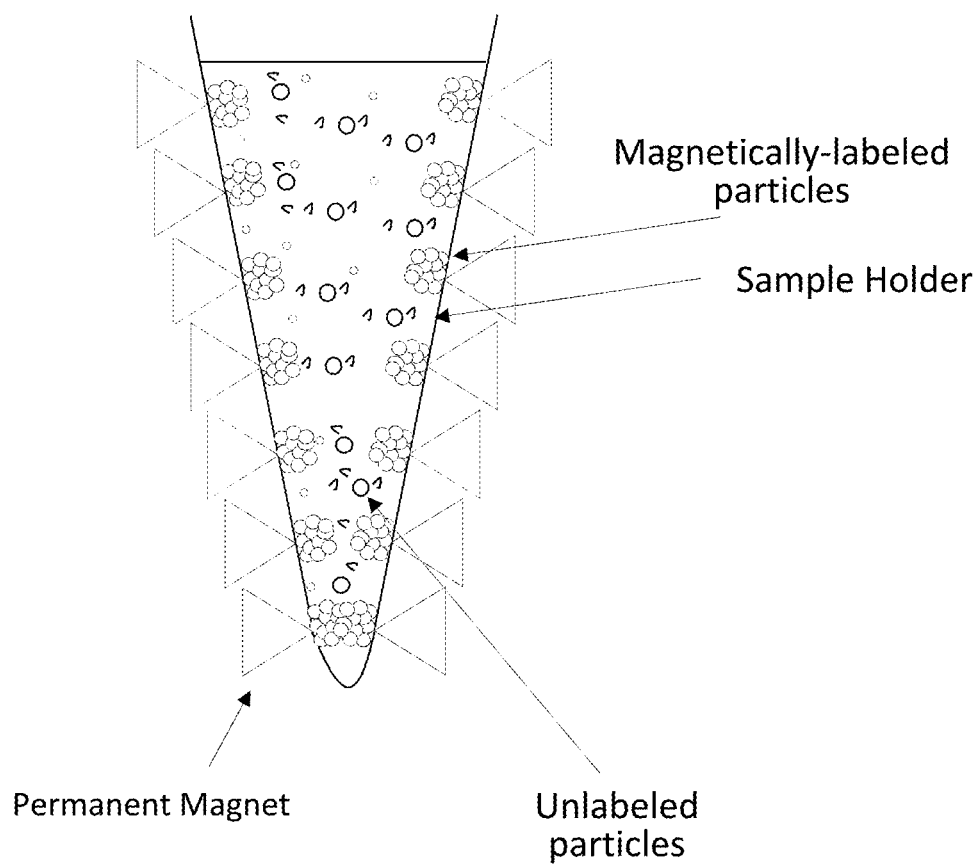

FIGS. 2A and 2B are schematic drawings of a device that includes a permanent magnet with sharp features that surrounds a sample holder. A liquid containing a mixture of magnetic and unlabeled particles is within the sample holder. As the sample holder is placed within a housing that includes a receptacle for the sample holder and the magnet, the magnetic particles become immobilized at the edge of the sample holder near the sharp features of the magnet, which produces the strongest magnetic field gradient. The unlabeled particles are not attracted to the magnet and do not cluster near the sharp features of the magnet.

Once the magnetic particles become immobilized in the sample holder near the magnetic source, the liquid containing unlabeled particles can be removed, e.g., by pipetting or decanting, thereby separating the magnetic particles from the unlabeled particles. The magnetic particles can be resuspended in a liquid to produce a sample enriched in the magnetic particles. The magnetic separation can be repeated multiple times to continuously enrich the sample for the magnetic particles.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Other embodiments are in the claims.

The invention claimed is:

1. A device for magnetic separation comprising:
    (a) a housing comprising a receptacle for a sample holder; and
    (b) a magnetic source surrounding at least 60% of a circumference of the receptacle and comprising a plurality of features comprising a corner radius of less than about 1 mm or producing a magnetic gradient of at least about 100,000 T/m, wherein the magnetic source is operably connected to the receptacle.

2. The device of claim 1, wherein the sample holder has a volume of less than about 10,000 μL.

3. The device of claim 2, wherein the volume is less than about 1,000 μL.

4. The device of claim 1, wherein the device comprises a plurality of the magnetic sources and/or a plurality of the receptacles.

5. The device of claim 1, wherein the magnetic source is removably attached to the housing.

6. A method for magnetic separation comprising:
    (a) providing the device of claim 1 and the sample holder, wherein the sample holder comprises a liquid comprising suspended magnetic particles; and
    (b) placing the sample holder in the receptacle, wherein the magnetic particles are immobilized at a location in the sample.

7. The method of claim 6, further comprising (c) removing the liquid from the sample holder and/or (d) resuspending the magnetic particles in a second liquid.

8. The method of claim 7, wherein removing the liquid comprises decanting, suctioning, or pipetting the liquid from the sample holder or wherein steps (c) and/or (d) are repeated one or more times.

9. A device for magnetic separation comprising:
    (a) a vessel comprising a lumen with an inlet and an outlet; and
    (b) a magnetic source surrounding at least 60% of a circumference of the lumen and disposed to exert a magnetic field in the lumen.

10. The device of claim 9, further comprising an outer vessel in which the vessel is disposed, wherein fluid passing through the outlet is captured in the outer vessel.

11. The device of claim 9, further comprising:
    a filter positioned in the lumen at or upstream of the outlet and configured to trap particles of a predetermined size.

12. The device of claim 11, wherein the filter is disposed at an angle relative to a horizontal cross-section of the lumen.

13. The device of claim 10, wherein the outer vessel has a volume of less than about 10,000 μL.

14. The device of claim 10, wherein the device comprises a plurality of the vessels, each of the vessels configured to fit within a corresponding outer vessel.

15. The device of claim 14, wherein the device comprises 8, 12, 16, 24, 32, 64, 96, 128, 256, or 396 of the vessels.

16. The device of claim 9, wherein the magnetic source is removably attached to the vessel.

17. A method for magnetic separation comprising:
    (a) providing the device of claim 9; and
    (b) transporting a liquid including suspended magnetic particles in the lumen so that the magnetic particles are immobilized at a location adjacent to the magnetic source.

18. A kit comprising:
    (a) a vessel comprising a lumen with an inlet and an outlet;
    (b) an outer vessel; and
    (c) a magnetic source surrounding at least 60% of a circumference of the lumen and disposed to exert a magnetic field in the lumen.

19. The device of claim 9, further comprising a baffle disposed at an angle relative to a horizontal cross-section of the lumen.

* * * * *